(12) United States Patent
Takeuchi et al.

(10) Patent No.: US 8,859,844 B2
(45) Date of Patent: Oct. 14, 2014

(54) SANITARY NAPKIN WITH A TOW FIBER ASSEMBLY

(75) Inventors: Tomonari Takeuchi, Tochigi (JP); Satoko Konawa, Tochigi (JP); Keisuke Ebitsuka, Tochigi (JP); Tomotsugu Matsui, Ehime (JP)

(73) Assignee: Diao Paper Corporation, Ehime (JP)

( * ) Notice: Subject to any disclaimer, the term of this patent is extended or adjusted under 35 U.S.C. 154(b) by 2150 days.

(21) Appl. No.: 11/631,226

(22) PCT Filed: Jun. 30, 2005

(86) PCT No.: PCT/JP2005/012131
§ 371 (c)(1),
(2), (4) Date: Jan. 22, 2008

(87) PCT Pub. No.: WO2006/004018
PCT Pub. Date: Jan. 12, 2006

(65) Prior Publication Data
US 2009/0247977 A1    Oct. 1, 2009

(30) Foreign Application Priority Data

Jun. 30, 2004  (JP) ................. 2004-194874
Jun. 30, 2004  (JP) ................. 2004-194876
Nov. 18, 2004  (JP) ................. 2004-335096
Feb. 8, 2005   (JP) ................. 2005-031662

(51) Int. Cl.
A61F 13/538    (2006.01)
A61F 13/512    (2006.01)
A61F 13/511    (2006.01)

(52) U.S. Cl.
CPC .......... *A61F 13/511* (2013.01); *A61F 13/51104* (2013.01); *A61F 2013/51178* (2013.01); *A61F 13/5116* (2013.01)
USPC .................................. 604/384; 604/378

(58) Field of Classification Search
CPC .......... A61F 13/5116; A61F 13/51104; A61F 2013/51165; A61F 2013/51178
USPC .................................................. 604/384
See application file for complete search history.

(56) References Cited

U.S. PATENT DOCUMENTS 3,507,943 A * 4/1970 Such et al. ............... 264/103
3,929,135 A * 12/1975 Thompson ............. 604/385.08
(Continued)

FOREIGN PATENT DOCUMENTS

CN    2258390 Y    7/1997
CN    1342446 A    4/2002
(Continued)

OTHER PUBLICATIONS

Supplementary European Search Report for corresponding application EP 05765331, having a completion date of Feb. 9, 2011.

*Primary Examiner* — Melanie Hand
*Assistant Examiner* — Paula L Craig
(74) *Attorney, Agent, or Firm* — Andrus Intellectual Property Law, LLP

(57) ABSTRACT

To provide a body fluid absorbent article having a face sheet 1, a body fluid permeable member 20 including an assembly of fibers in tows, a body fluid retainable absorbent element AB in this order, and a face-side second sheet 10, which is interposed between the above face sheet 1 and the above body fluid permeable member 20 with such a positional relation that the above face-side second sheet 10 is at least partly superposed on the above body fluid permeable member 20; and embossing is carried out integrally on the above face sheet 1 and the above face-side second sheet 10 while embossing is not carried out on the above body fluid permeable member 20.

3 Claims, 44 Drawing Sheets

(56) References Cited

U.S. PATENT DOCUMENTS

| | | | |
|---|---|---|---|
| 4,323,068 A * | 4/1982 | Aziz | 604/370 |
| 4,323,069 A * | 4/1982 | Ahr et al. | 604/378 |
| 4,342,314 A * | 8/1982 | Radel et al. | 604/370 |
| 4,360,022 A * | 11/1982 | Usami et al. | 604/368 |
| 4,392,862 A | 7/1983 | Marsan et al. | |
| 4,397,644 A * | 8/1983 | Matthews et al. | 604/378 |
| 4,726,976 A * | 2/1988 | Karami et al. | 428/137 |
| 4,910,064 A * | 3/1990 | Sabee | 428/113 |
| 5,257,982 A * | 11/1993 | Cohen et al. | 604/378 |
| 5,368,909 A * | 11/1994 | Langdon et al. | 428/137 |
| 5,368,910 A * | 11/1994 | Langdon | 428/137 |
| 5,370,764 A * | 12/1994 | Alikhan | 156/553 |
| 5,387,208 A * | 2/1995 | Ashton et al. | 604/378 |
| 5,449,352 A * | 9/1995 | Nishino et al. | 604/383 |
| 5,466,513 A * | 11/1995 | Wanek et al. | 428/218 |
| H1565 H * | 7/1996 | Brodof et al. | 604/368 |
| 5,556,392 A * | 9/1996 | Koczab | 604/378 |
| 5,613,960 A * | 3/1997 | Mizutani | 604/365 |
| 5,647,863 A * | 7/1997 | Hammons et al. | 604/378 |
| 5,674,211 A * | 10/1997 | Ekdahl | 604/383 |
| 5,695,486 A * | 12/1997 | Broughton et al. | 604/374 |
| 5,913,850 A * | 6/1999 | D'Alessio et al. | 604/378 |
| 5,972,505 A | 10/1999 | Phillips et al. | |
| 5,989,478 A * | 11/1999 | Ouellette et al. | 264/468 |
| 6,027,483 A * | 2/2000 | Chappell et al. | 604/385.01 |
| 6,168,849 B1 * | 1/2001 | Braverman et al. | 428/137 |
| 6,511,566 B1 * | 1/2003 | Wessel et al. | 156/181 |
| 6,610,039 B1 * | 8/2003 | Wilhelm et al. | 604/385.27 |
| 6,610,391 B2 * | 8/2003 | Molee | 428/212 |
| 6,646,180 B1 | 11/2003 | Chmielewski | |
| 6,660,902 B2 | 12/2003 | Widlund et al. | |
| 7,303,808 B2 * | 12/2007 | Taneichi et al. | 428/198 |
| 7,468,114 B2 * | 12/2008 | Sato et al. | 156/209 |
| 7,717,150 B2 * | 5/2010 | Manabe et al. | 156/497 |
| 7,722,588 B1 * | 5/2010 | Johnson et al. | 604/385.18 |
| 8,466,334 B2 * | 6/2013 | Takeuchi et al. | 604/367 |
| 2002/0072724 A1 * | 6/2002 | Furuya et al. | 604/367 |
| 2002/0115974 A1 * | 8/2002 | Hermansson et al. | 604/385.01 |
| 2002/0169430 A1 * | 11/2002 | Kirk et al. | 604/378 |
| 2003/0105442 A1 * | 6/2003 | Johnston et al. | 604/368 |
| 2003/0134559 A1 | 7/2003 | Delzer et al. | |
| 2003/0143376 A1 * | 7/2003 | Toyoshima et al. | 428/156 |
| 2004/0024375 A1 | 2/2004 | Litvay | |
| 2004/0140047 A1 * | 7/2004 | Sato et al. | 156/205 |
| 2004/0204697 A1 * | 10/2004 | Litvay | 604/367 |
| 2004/0265534 A1 * | 12/2004 | Curro et al. | 428/92 |
| 2008/0038504 A1 * | 2/2008 | Manabe et al. | 428/71 |
| 2008/0044616 A1 * | 2/2008 | Hanao et al. | 428/68 |
| 2008/0262459 A1 * | 10/2008 | Kamoto et al. | 604/375 |
| 2008/0312627 A1 * | 12/2008 | Takeuchi et al. | 604/375 |
| 2009/0004435 A1 * | 1/2009 | Hanao et al. | 428/156 |

FOREIGN PATENT DOCUMENTS

| | | |
|---|---|---|
| CN | 1372451 A | 10/2002 |
| CN | 1507336 A | 6/2004 |
| JP | 57-205506 | 12/1982 |
| JP | H4 504285 A | 7/1992 |
| JP | H5-277147 A | 10/1993 |
| JP | 3025258 U | 3/1996 |
| JP | 9-117471 A | 5/1997 |
| JP | H10 118113 A | 5/1998 |
| JP | 10-192342 | 7/1998 |
| JP | 10-192342 A | 7/1998 |
| JP | H11-081116 A | 3/1999 |
| JP | 2000-015093 A | 1/2000 |
| JP | 2000-333992 A | 12/2000 |
| JP | 2001-214399 A | 8/2001 |
| JP | 2001-231815 A | 8/2001 |
| JP | 2001-524350 A | 12/2001 |
| JP | 2002 65743 A | 3/2002 |
| JP | 2002-509764 A | 4/2002 |
| JP | 2002-177330 A | 6/2002 |
| JP | 2002-282304 A | 10/2002 |
| JP | 2002-291804 A | 10/2002 |
| JP | 2003-33397 A | 2/2003 |
| JP | 2003-033398 A | 2/2003 |
| JP | 2003-70820 A | 3/2003 |
| JP | 2003-088555 A | 3/2003 |
| JP | 2003 144489 A | 5/2003 |
| JP | 2003-190210 A | 7/2003 |
| JP | 2003-192732 A | 7/2003 |
| JP | 2004-41339 A | 2/2004 |
| JP | 2004-129924 | 4/2004 |
| WO | 93/02235 A1 | 2/1993 |
| WO | 99/27876 A1 | 6/1999 |
| WO | 99/27879 A2 | 6/1999 |
| WO | WO-99/27876 | 6/1999 |
| WO | 99/49826 A1 | 10/1999 |
| WO | WO 01/17475 A1 * | 3/2001 |
| WO | 02/091975 A1 | 11/2002 |
| WO | 2004/017883 A1 | 3/2004 |

\* cited by examiner

FIG. 49
(a)
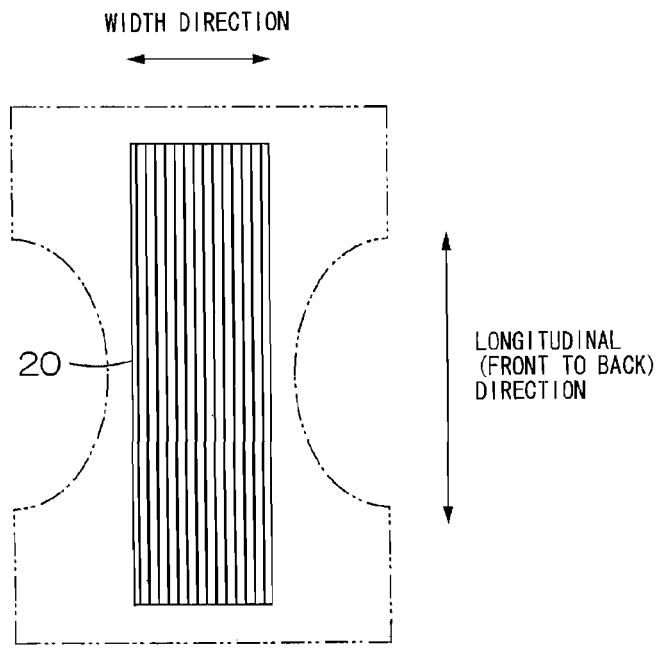
(c)
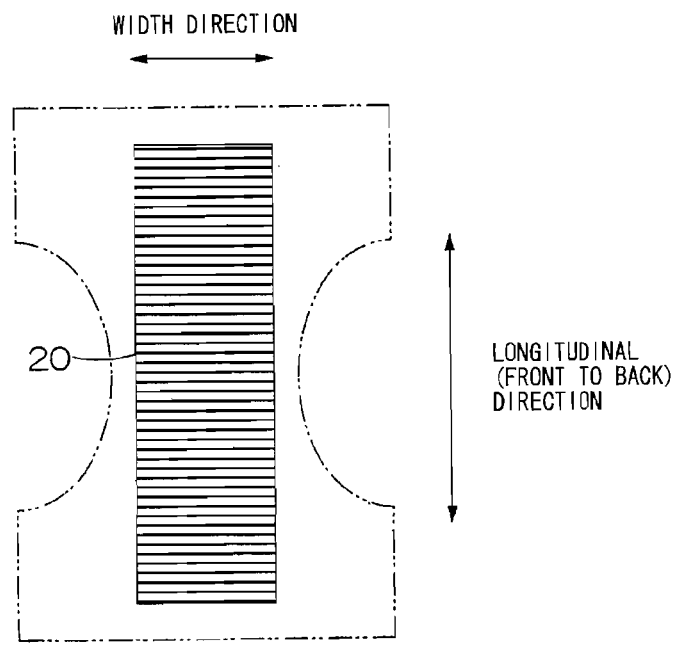

SANITARY NAPKIN WITH A TOW FIBER ASSEMBLY

This application is a national phase of PCT/JP2005/012131 filed Jun. 30, 2005, and claims priority to Japanese application 2004-194876 filed Jun. 30, 2004, Japanese application 2004-194874 filed Jun. 30, 2004, Japanese application 2004-335096 filed Nov. 18, 2004, and Japanese application 2005-031662 filed Feb. 8, 2005.

TECHNICAL FIELD

The invention relates to body fluid absorbent articles, which can be applied articles such as disposable diapers, sanitary napkins, urine pads, incontinence pads or the like. Particularly, this invention preferably relates to sanitary napkins.

BACKGROUND OF THE INVENTION

Each body fluid absorbent article such as a disposable diaper, a sanitary napkin, a urine pad, an incontinence pad or the like has generally a body fluid absorbent article provided with a face sheet and a body fluid retainable absorbent element disposed under the face sheet. Such body fluid retainable absorbent element is conventionally fabricated from pulp e.g., flocculent pulp or synthetic pulp or fluff pulp, into which absorbent polymer is mixed in the form of e.g., particles. The absorbent element fabricated like this absorbs the body fluid with rather low speed. Thus, before the body fluid is completely absorbed into the absorbent element, the body fluid is moved to reach the ends or edges of the article, which may cause the body fluid leakage at the ends or edges of the article.

To cope with it, in these days, as a so-called second sheet, e.g., a non-woven sheet is disposed between the face sheet and the body fluid retainable absorbent element. This second sheet is generally used to promote the quick permeating of the body fluid toward the absorbent element-side before reaching the ends or edges of the article, which leads the function of protecting against the leakage of the body fluid at the ends or edges of the article.

On the other hand, Patent Citation 1 discloses a second sheet formed by bonding an upper layer and lower layer, each of which has continuous fibers in tows, through bonding patterns (See e.g., Patent Citation 1). This second sheet fulfills its own function, which is more improved than those of the conventional second sheets.

However, the following problem is found. Precisely, when the upper and lower layer, each of which has continuous fibers in tows, are bonded through bonding embossed patterns, the space between the fibers is decreased due to the embossing. This situation blocks the permeating of the body fluid, besides, damages the ability to retain temporarily the body fluid coming into the second sheet. Finally, this second sheet also cannot fulfill sufficiently its own inherent function.

[Patent Citation 1] Published Japanese translation of PCT international publication for patent application No. 2001-524399

DISCLOSURE OF INVENTION

Problem to be solved by the Invention

The main problem to be solved by the present invention is to provide a second sheet, which fulfills enough its function, while the "sticking" caused by the conventional second sheet is prevented by the embossing applied on a face sheet.

SUMMARY OF THE INVENTION

Means for Solving Problem

The present invention solving this problem is as follows.
[Invention Claimed in Claim 1]
A body fluid absorbent article having a face sheet, a body fluid permeable member including an assembly of fibers in tows, and a body fluid retainable absorbent element in this order, comprising
a face-side second sheet, which is interposed between said face sheet and said body fluid permeable member with such a positional relation that said face-side second sheet is at least partly superposed on said body fluid permeable member; and
said face sheet and said face-side second sheet, on which embossing is carried out integrally, and the above body fluid permeable member, on which embossing is not carried out.
[Invention Claimed in Claim 2]
A body fluid absorbent article as defined in Claim 1, wherein both areas of said face-side second sheet and said fluid permeable member are smaller than the both areas of said face sheet and of said body fluid retainable absorbent element.
[Invention Claimed in Claim 3]
A body fluid absorbent article as defined in Claim 1 or 2 wherein the constituent fiber of said assembly of fibers in tows is cellulose acetate fiber.
[Invention Claimed in Claim 4]
A producing method of a body fluid absorbent article having a face sheet, a body fluid permeable member including an assembly of fibers in tows, and a body fluid retainable absorbent element in this order,
wherein said article comprising a face-side second sheet, which is interposed between said face sheet and said body fluid permeable member with such a positional relation that said face-side second sheet is at least partly superposed on said body fluid permeable member, and
said method comprising steps of
carrying out embossing integrally on said face sheet and said face-side second sheet, on the resultant embossed sheets, placing said body fluid permeable member, and placing said body fluid retainable absorbent element in this order.

Effect of the Invention

If the face sheet is an even surface, when the wearer's skin contacts with the face sheet, particularly in the case of wet skin due to the sweat, the face sheet sticks to the skin, resulting in extremely bad feeling for the wearer. In the present invention, since the embossing is carried out on the face sheet so as to form depressed portions on this sheet, the contact area between the skin and the face sheet is decreased so that such sticking can be prevented. Further, according to the present invention, the embossing is carried out integrally on the face sheet and the face-side second sheet. From the viewpoint of feeling for the wearer, the face sheet should be flexible as much as possible. In order to attain this flexibility, the face sheet is formed so as to be thin, but it is difficult to carry out the embossing on the thin sheet to form large or deep depressed portions. Contrary to this, by carrying out the embossing integrally on the face sheet and the face-side second sheet, it is possible to form large or deep depressed portions as desired.

A conventional second sheet is commonly fabricated from a non-woven fabric. Then, in the present invention, the face-side second sheet also may be fabricated from non-woven fabric. Thus such face-side second sheet promotes the body fluid permeating and protects against the body fluid reversing in the same manner as the conventional second sheet.

In the present invention, at the under surface-side of the face-side second sheet, the body fluid permeable member including the assembly of fibers in tows and the body fluid retainable absorbent element are disposed in this order.

Accordingly, the body fluid permeates through the face sheet and the face-side second sheet to reach the body fluid permeable member including the assembly of fibers in tows. Then, since this member has large space between the fibers, the body fluid can permeate smoothly there, besides, in this member, since the fibers are arranged substantially in the uniform direction, the body fluid can be diffused smoothly. Finally, the body fluid can be absorbed sufficiently into the body fluid retainable absorbent element.

Further, in the body fluid permeable member including the assembly of fibers in tows, the space volume formed between the fibers is enough large to have high cushioning property.

BEST MODE FOR CARRYING OUT THE INVENTION

Now, the embodiment of the present invention will be explained closely with reference to sanitary napkins shown in the accompanied drawings.

[Embodiment of Sanitary Napkin]

FIG. 1 shows the body fluid absorbing face of the developed sanitary napkin, while FIG. 2 shows with exaggeration the cross section taken on line 2-2 of FIG. 1. This sanitary napkin comprises the back sheet 2, which is for example, impermeable and which is fabricated from a polyethylene sheet, a polypropylene sheet, a material formed by superposing the external non-woven fabric and impermeable sheet or the like, and the permeable face sheet 1, through which menstrual blood, vaginal discharge or the like permeates quickly. Then, the body fluid retainable absorbent element AB is disposed between the permeable face sheet 1 and the back sheet 2 and at the same time, in the middle portion of this article in its width direction. This absorbent element AB includes the absorbent core 4, which is fabricated from flocculent pulp, synthetic pulp or the like, and as desired, the covering sheet 5, which covers the absorbent core 4 for keep its shape and for improving its diffusibility. Thus, as a main body fulfilling the function of receiving, absorbing and retaining the body fluid, these parts are adapted to locate at the center of this article.

DETAILED DESCRIPTION OF THE INVENTION

The face sheet 1 is shaped to have larger area than that of the absorbent element AB and is disposed to cover the whole surface of the absorbent element AB. The impermeable back sheet 2 is shaped so as to contour this article on the plan view. Then, the both side portions of the back sheet 2 are extended beyond the both side edges of the absorbent core AB. Both side sheets 6, 6, which are fabricated from an impermeable or poorly permeable non-woven fabric or the like, are jointed to and laminated on the both extended side portions of the back sheet so as to cover totally there. As the method for jointing, there can be used adhesive bonding with hot melt adhesive, ultrasonic sealing, heat seal, heat press or the combination of these methods.

As shown in the drawings, it is preferable that the peripheral portion of the article, concretely, the opposite free side edges of the laminating portions comprised by the back sheet 2 and the side sheets 6, 6, as well as the front end portion and the back end portion of the permeable face sheet 1 and those of impermeable back sheet 2 are bonded surely by heat seal b1, b2, respectively.

According to this embodiment, in the laminating portions comprised by the impermeable back sheet 2 and the side sheets 6, 6, particularly, the crotch zones and the hip zones are extended outwardly and largely so as to form flap portions F1, F1 for folding around the edges of the garment and hip cover flap portions F2, F2. However, these flap portions may be provided as desired, and they may be omitted.

Further, according to the embodiment shown in the drawings, in the opposite side portions of the article, the barriers 30, 30 for protecting against the side leakage, which are extended in the longitudinal direction of the article, may be provided. In this embodiment shown in the drawing, the other side edges of the side sheets 6, 6 are free and at these free edge-sides, elastically expansible members 32, 32 are fixed along the longitudinal direction of the article in the elongated state. Then, the front end portions and back end portions of the side sheets 6, 6 in their longitudinal directions are folded to superpose and joint each other. On the other hand, intermediate portions of the side sheets 6, 6 are not jointed. In this way, in use of the article, as shown in FIG. 2, the both intermediate portions of the side sheets 6, 6 stand due to the contracting force caused by the elastically expansible members 32, 32. Finally, these intermediate portions fulfill the function of the barriers 30, 30 for protecting the side leakage of menstrual blood.

In the present invention, as shown in FIG. 2, is provided the sanitary napkin, which comprises the face sheet 1, the body fluid permeable member 20 including the assembly of fibers in tows and the body fluid retainable absorbent element AB in this order.

Further, a face-side second sheet 10, which is interposed between the face sheet 1 and the body fluid permeable member 20 with such a positional relation that the face-side second sheet 10 is at least partly superposed on the body fluid permeable member 20; and the embossing E is applied integrally on the face sheet 1 and the face-side second sheet 10 while the embossing is not applied on the body fluid permeable member 20.

In these drawings, each depressed portion formed by the embossing E has the shape of a circle, but it may have another shape desirably such as an ellipse, a quadrangle or the like. Further, in these drawings, the depressed portions formed by the embossing E are scattered, but continuous groove-shaped portion is also possible. By arranging the continuous groove-shaped portion in the longitudinal direction of the article, the body fluid can be induced or diffused along the embossed groove, leading to the high absorbing capacity for the body fluid. Moreover, plural continuous groove-shaped depressions can be formed in the longitudinal direction of the article so as to space each other in its longitudinal direction or in its width direction. Then, it is preferable that the whole area of the top face of the body fluid permeable member 20 covers 70% or more of the area occupied by the embossed portion (the area occupied by the total form of depressed portions in case of scattered depressed portions).

Additionally, the both areas of the face-side second sheet 10 and of the body fluid permeable member 20 are smaller than the both areas of the face sheet 1 and of the body fluid retainable absorbent element AB.

The preferable constituent fiber of the assembly of fibers in tows is cellulose acetate fiber.

If the face sheet 1 is an even surface, when the wearer's skin contacts with the face sheet, particularly in the case of wet skin due to the sweat, the face sheet sticks to the skin, resulting in extremely bad feeling for the wearer. However, since the embossing E is applied on the face sheet 1 so as to form depressed portions on the face sheet 1, the contact area between the skin and the face sheet is decreased so that such sticking can be prevented. Further, the embossing E is applied integrally on the face sheet 1 and the face-side second sheet 10. By the integrally embossing for the both of the face sheet 1 and the face-side second sheet 10, depressed portions each having the desirable area and desirable depth can be formed. Additionally, as the face-side second sheet 10, by using e.g., a non-woven fabric, which is used commonly for the conventional second sheet, the face-side second sheet promotes the body fluid permeating and protects against the body fluid reversing.

At the under surface-side of the face-side second sheet 10, the body fluid permeable member 20 including the assembly of fibers in tows and the body fluid retainable absorbent element 4 are disposed in this order. In such configuration, the body fluid permeates through the face sheet 1 and the face-side second sheet 10 to reach the body fluid permeable member 20 including the assembly of fibers in tows. Then, since this member 20 has large space between the fibers, the body fluid can permeate smoothly through this member 20, besides, in this member 20, since the fibers are arranged substantially in the uniform direction, the body fluid can be diffused smoothly. Finally, the body fluid can be absorbed sufficiently into the body fluid retainable absorbent element AB.

As shown in the enlarged drawing of FIG. 2, it is preferable that the embossing is carried out on the face-side second sheet 10 so as to project downwardly from the under surface of the face-side second sheet 10. Further, it is more preferable that these projected portions (jogs) from the under surface of the face-side second sheet 10 substantially contact to the body fluid permeable member 20 including the assembly of fibers in tows.

In such configuration, the body fluid tends to permeate mainly through the embossing E toward the under surface-side of the face-side second sheet 10. That is to say, it is difficult for the body fluid to remain on the upper surface of the face sheet 1 at its not depressed portions. Thus, the sticking can be prevented. Further, projected portions (jogs) from the under surface of the face-side second sheet 10 substantially contact to the body fluid permeable member 20 including the assembly of fibers in tows. Accordingly, the body fluid, which tends to permeate mainly through the embossing E toward the under surface-side of the face-side second sheet 10, moves quickly to the body fluid permeable member 20. Additionally, since this member 20 has high body fluid permeability, the body fluid can permeate quickly through this member 20 to reach the absorbent element AB. Now, the specific advantage given by the embodiment shown in the drawing will be explained. If embossing were carried out also on the body fluid permeable member 20, thus resultant compressed portions of the body fluid permeable member 20 would have the high density. In this situation, even if the projected portions (jogs), which are projected downwardly from the under surface of the face-side second sheet 10, substantially contact to the body fluid permeable member 20, since these projected portions have high density, the body fluid would not penetrate quickly from these projected portions into the permeable member 20, thereby the body fluid would not penetrate quickly to the absorbent element AB. Finally, the absorption speed would be decreased. It is clear from this explanation that the embossing according to the present invention is specifically preferable.

In order to produce such sanitary napkin, as shown in FIG. 3, first, the face sheet 1 is unrolled from its unreeler, while the side sheet 6 is unrolled from its unreeler as desired. Next, the face-side second sheet 10 is unrolled from its unreeler. Then, embossing is carried out integrally on the face sheet 1 and the face-side second sheet 10 with the emboss roller 50. This emboss roller 50 has a preferable configuration such as a combination of engraved roller and rubber covered roller, a mutual engagement of two engraved rollers, or the like, and what is required for the emboss roller 50 is at least that it can emboss the face sheet 1.

Further, the body fluid permeable member 20 including the assembly of fibers in tows is held by and unrolled from the suction roller to be supplied to the surface of the integrally embossed face sheet 1 and face-side second sheet 10. After that, the flocculent pulp for fabricating the absorbent core 4 is unrolled. Then, these are laminated. Directly following this, or in suitable steps, thus laminated substance is cut and treated individually so that the sanitary napkins are obtained as articles.

[Material and the Like of Each Member]

Now, the materials will be explained in order.

(Assembly of Fibers in Tows)

An assembly of fibers in tows (the assembly is produced from the tows as the raw material) means tows (fiber bundles), each of which is comprised by fibers. As the fiber, there are for example, polysaccharide or the derivatives thereof (cellulose, cellulose ester, chitin, chitosan or the like), synthetic polymer (polyethylene, polypropylene, polyamide, polyester, poly lactamide, polyvinyl acetate or the like), and the like can be used. Above all the cellulose ester and cellulose are preferable.

Further, as the cellulose, cellulose derived from plant such as cotton, linter, wood pulp or the like as well as bacterial cellulose may be used. Regenerated cellulose may be also used, and closely as the regenerated cellulose, a spun regenerated cellulosic fiber may be used. The shape and size of the cellulose can be selected from the wide range, from substantially infinite length of the continuous single fiber to the length of about few millimeters to few centimeters (for example, 1 mm to 5 cm) in the major axis of fiber or to the length of about few micron (for example, 1 to 100 µm) in the particle size of fine powder. The cellulose may be fibrillated such as beaten pulp or the like.

On the other hand, as the cellulose ester, there can be listed esters of organic acids such as cellulose acetate, cellulose butyrate, cellulose propionate or the like; esters of mix acids such as cellulose acetate propionate, cellulose acetate butyrate, cellulose acetate phthalate, cellulose acetate nitrate or the like; and the derivatives of the cellulose ester such as polycaprolactone grafted cellulose ester or the like. The cellulose esters can be used alone or in two or more kinds thereof. The viscosity average degree of polymerization of the cellulose ester is for example, about 50 to 900 and preferably about 200 to 800. Then the average degree of substitution of cellulose ester is for example, about 1.5 to 3.0 (for example, 2 to 3).

The average degree of polymerization of the cellulose esters may be for example, about 10 to 1000, preferably about 50 to 900 and more preferably about 200 to 800. Then, the average degree of substitution of cellulose ester may be for example, about 1 to 3, preferably about 1 to 2.15, more preferably about 1.1 to 2.0. The average degree of substitution of cellulose ester can be determined from the viewpoint of improving the biodegradability.

As the cellulose ester, esters of organic acids (for example, the ester with organic acid having the carbon number of about 2 to 4) are preferable and cellulose acetate is more preferable. This is because the cellulose acetate is particularly suitable for increasing the absorbed volume of body fluid due to its high porosity. Concretely, in the case of body fluid permeable absorbent member 52, its porosity (the space volume/the absorbent member volume) can be preferably 60 to 85%, more preferably 75 to 85%.

The acetylation degree of the cellulose acetate is, in many cases, 43 to 62%. Particularly, it is more preferably 30 to 50%, because this range causes high biodegradability.

To the fibers in tows, several kinds of addition agents may be added, such as heat stabilizer, colorant, oil solution, yield improving agent, whiteness improving agent or the like.

The fineness of each fiber may be for example, 1 to 16 denier, preferably 1 to 10 denier, more preferably 2 to 8 denier. The fiber may be uncrimped, but the fiber is preferably crimped. The degree of crimp of the crimped fiber may be for example, 5 to 75, preferably 10 to 50, more preferably 15 to 50 pieces per 1 inch (2.54 cm). In many cases, uniformly crimped fibers are used. By using the crimped fibers, bulky and lightweight absorbent member can be produced, as well as high integrity of the tows can be produced easily due to the tangle of the fibers.

The cross sectional shape of the fiber is not specifically limited and may be selected from the group including circle, ellipse, irregular shape (e.g., Y-shaped, X-shaped, I-shaped, R-shaped or the like) and the like, further, the hollow type fiber may be possible.

The fibers can be used in the tows (fiber bundles), each of which is formed by bundling for example, about 3,000 to 1,000,000, preferably about 5,000 to 1,000,000, single fibers. It is preferable that about 3,000 to 1,000,000 continuous single fibers are gathered to the fiber bundle.

When the body fluid is repeatedly absorbed into the assembly of fibers in tows, since the tangle of the fibers is weak, the spaces between the fibers should be treated so as not to collapse. Therefore, the binder, which can adhere or fuse the fibers at their mutual contacting portions, can be used preferably.

As the binder used here, there can be listed ester plasticizer such as triacetin, triethylene glycol diacetate, triethylene glycol dipropionate, dibutyl phthalate, dimethoxyethyl phthalate, triethyl ester citrate or the like as well as several kinds of resin adhesives, specifically thermoplastic resin.

When the thermoplastic resin is fused • solidified, the adhesiveness is appeared. This resin includes water-insoluble, water-hardly soluble resin and water-soluble resin. If desired, these water-insoluble, water-hardly soluble resin and water-soluble resin can be jointly used.

As the water-insoluble or water-hardly soluble resin used here, there can be listed olefin monopolymer or olefin copolymer such as polyethylene, polypropylene, ethylene-propylene copolymer, ethylene-vinyl acetate copolymer or the like, acrylic resin such as polyvinyl acetate, polymethyl methacrylate, methyl methacrylate-acrylic ester copolymer, copolymer of (meta) acrylic monomer and styrene monomer or the like, styrene polymer such as polyvinyl chloride, vinyl acetate-vinyl chloride copolymer, polystyrene, copolymer of styrene monomer and (meta)acrylic monomer, modifiable polyester, polyamide such as, nylon 11, nylon 12, nylon 610, nylon 612 or the like, rosin derivatives (e.g., rosin ester or the like), hydrocarbon resin (e.g., terpene resin, dicyclopentadiene resin, petroleum resin or the like), hydrogenated hydrocarbon resin, and so on. These thermoplastic resins can be used alone or in two or more kinds thereof.

As the water-soluble resin used here, there can be listed various kinds of water-soluble polymer, for example, water-soluble vinyl resin such as polyvinyl alcohol, polyvinyl pyrrolidone, polyvinyl ether, copolymer of vinyl monomer and copolymerizable monomer having carboxyl group, sulfonic group or the salt thereof or the like, water-soluble acrylic resin, polyalkylene oxide, water-soluble polyester, water-soluble polyamide and the like. These water-soluble resins can be used alone or in two or more kinds thereof.

Several kinds of additives can be added to the thermoplastic resin. There are for example, stabilizing agent such as anti-oxidizing agent, ultraviolet absorber or the like, filler, plasticizer, antiseptic agent, mildewproofing agent and the like.

In using the binder, as shown in FIG. 11, the binder may be added to the whole of the assembly 20 of fibers in tows. Precisely, the binder is added uniformly to the whole of external surface, under surface, inside and outside of the assembly 20 of fibers so as to reinforce totally adhesion degree or fusion degree of the fibers in their contacting portions in the form of line or dot. The tow can be used as the good absorber showing the high level when the body fluid first permeates, because the tow is porous and bulky. However, the body fluid once penetrates through the tow, the tow tends to lose its stiffness. In this way, after the tow loses its stiffness, its porous property is decreased. Thus, the body fluid permeability is remarkably lowered. That is, it is so difficult for the fibers in tows to keep the both of porous and body fluid high permeability. In this regard, by adding the binder, even after the body fluid is absorbed into the assembly 20 of fibers, its stiffness can be maintained and thereby the body fluid permeability can be improved.

Further, when the binder is used in the assembly of fibers, according to the adjustment of the added amount of this binder, the adhesion degree or fusion degree of the fibers are made different between or among at least two zones. In the embodiment of the assembly 20 of fibers shown in FIG. 12, the adhesion degree or fusion degree of the fibers in their contacting portions in the form of line or dot at the middle portion in the width direction is stronger than those at the both side portions in the width direction by adjusting the added amount of binder to the middle portion so as to be larger than the added amount of binder to the both side portions. In each drawing, the zones, which are different in the added amount of binder, are designated by $A_1$, $A_2$. In this case, the added amount of binder in $A_1$ is larger than that in $A_2$. For example, this assembly 20 of fibers is incorporated into a body fluid absorbent article such as a sanitary napkin or the like so that the longitudinal direction of the assembly 20 of fibers corresponds to the longitudinal direction of the absorbent article. Thus, in this absorbent article, the body fluid is absorbed quickly at the zone near the wearer's excretory organ, for example, at the zone into which discharged menstrual blood is absorbed. Additionally, this absorbent article offers the stiffness at the both side portions as well as protection against the side leakage.

In the embodiment shown in FIG. 13, the adhesion degrees or fusion degrees of the fibers in their contacting portions in the form of line or dot at the both side portions in the width direction are stronger than that at the middle portion in the width direction by adjusting the added amount of binder to the both side portions so as to be larger than the added amount of binder to the middle portion.

In the embodiment shown in FIG. 14, the adhesion degrees or fusion degrees of the fibers in their contacting portions in the form of line or dot at the front end portion and at the back end portion in the longitudinal direction of the assembly 20 of fibers are stronger than that at the intermediate portion in the longitudinal direction by adjusting the added amount of binder to the front end portion and to the back end portion so as to be larger than the added amount of binder to the intermediate portion. For example, the assembly of fibers 20 is incorporated into a body fluid absorbent article such as a sanitary napkin or the like so that the longitudinal direction of the assembly of fibers 20 corresponds to the longitudinal direction of the absorbent article. Thus, in this absorbent article, the body fluid permeates quickly at the zone near the wearer's excretory organ, for example, at the zone into which discharged menstrual blood is absorbed. Additionally, this absorbent article offers the stiffness at the front and back end portions as well as protection against the front and back leakage.

In the embodiment shown in FIG. 15, the adhesion degree or fusion degree of the fibers in their contacting portions in the form of line or dot at the surrounding portion of the assembly 20 of fibers is stronger than that at the surrounded portion by adjusting the added amount of binder to the surrounding portion so as to be larger than the added amount of binder to the surrounded portion. In other words, the added amount of binder is decreased only to the center portion of the assembly 20 of fibers. In this embodiment, for example, the assembly 20 of fibers is incorporated into a body fluid absorbent article such as a sanitary napkin or the like so that the longitudinal direction of the assembly 20 of fibers corresponds to the longitudinal direction of the absorbent article. Thus, in this absorbent article, the body fluid is absorbed quickly at the zone near the wearer's excretory organ, for example, at the zone into which discharged menstrual blood is absorbed, besides, the article offers stiffness at this zone. Additionally, this absorbent article offers the more reliable stiffness at the surrounding portion as well as protection against the front, back and side leakage.

FIGS. 16 to 20 are the cross sections, in the width direction, of the assembly 20 of fibers. In the embodiment shown in FIG. 16, the adhesion degrees or fusion degrees of the fibers in their contacting portions in the form of line or dot at the portion near the top face and at the portion near the bottom face are stronger than that at the sandwiched portion between the top face and the bottom face by adjusting the added amount of binder to the portion near the top face and to the portion near the bottom face so as to be larger than the added amount of binder to the sandwiched portion. This absorbent structure 20 offers stiffness at the portion near the top face, the portion near the bottom face and the sandwiched portion, specifically more reliable stiffness at the portion near the top face and the portion near the bottom face. Then, the body fluid can permeate repeatedly into this absorbent structure 20, and besides, the body fluid is hardly remained at the portion near the top face and the portion near the bottom face. In this way, this absorbent structure 20 forms an absorbent article, which gives an impression of cleanliness.

In the embodiment shown in FIG. 17, the adhesion degrees or fusion degrees of the fibers in their contacting portions in the form of line or dot at the portion near the top face, at the portion near the bottom face, and at the side end portions on the cross section in the width direction are stronger than that at the midst portion on the cross section in the width direction by adjusting the added amount of binder to the portion near the top face, to the portion near the bottom face and to the side end portions so as to be larger than the added amount of binder to the midst portion. This embodiment offers, addition to the advantages given by the embodiment shown in FIG. 16, the stiffness at the side end portions on the cross section in the width direction. Further, the body fluid can permeate quickly also at the side end portions.

In the embodiment shown in FIG. 18, the adhesion degree or fusion degree of the fibers in their contacting portions in the form of line or dot at the midst portion on the cross section in the width direction is stronger than that at the portion near the top face, at the portion near the bottom face, and at the side end portions on the cross section in the width direction by adjusting the added amount of binder to the midst portion so as to be larger than the added amount of the binder to the portion near the top face, to the portion near the bottom face and to the side end portions.

In the embodiment shown in FIG. 19, the adhesion degrees or fusion degrees of the fibers in their contacting portions in the form of line or dot at the side end portions on the cross section in the width direction are stronger than that at the midway portion on the cross section in the width direction by adjusting the added amount of binder to the side end portions so as to be larger than the added amount of the binder to the midway portion. This embodiment offers the stiffness at the side end portions on the cross section in the width direction.

In the embodiment shown in FIG. 20, the adhesion degree or fusion degree of the fibers in their contacting portions in the form of line or dot at the midway portion on the cross section in the width direction is stronger than that at the side end portions on the cross section in the width direction by adjusting the added amount of binder to the midway portion so as to be larger than the added amount of binder to the side end portions.

The relation between the embodiments shown in the plan views and those shown in the cross sections is not exclusive. That is to say, the conditions of the both embodiments can be put together within the permitted limits. For example, when the assembly of fibers has the embodiment shown in FIG. 12 on the plan view seen from the wearer-side, and at the same time it has the embodiment shown in FIG. 19 on the cross section in the width direction, it is needless to say that this assembly is included in the present invention.

The assembly of fibers can be produced from the tows as the material according to the conventional processes. The bale of tows of cellulose diacetate, which can be used preferably in the present invention, is available in the market from Celanese Chemicals, Ltd., Daicel Chemical Industries Ltd., and the like. In the bale of tows of cellulose diacetate, the density is about 0.5 g/cm$^3$ and the total weight is 400 to 600 kg.

In producing the assembly of fibers, the tow removed from the bale can be opened so as to be belt-shaped with preferable size and bulk as desired. The width of opened tow can be determined arbitrarily, can be for example, about 100 to 2000 mm, preferably about 150 to 1500 mm. The opening of the tow is preferable, because opening treatment facilitates the easy movement of the absorbent polymer. Further, the opening degree of tow is adjusted so that the porosity of the absorbent member can be preferably arranged.

As a method for opening the tow, there can be listed a method that a tow is applied to plural opening rolls, through which the tow is processed, and the tow is gradually widened; a method of opening tow by repeating the stretching (elongating) and relaxing (contracting) of tow; a method of widening• opening tow with compressed air and the like.

FIG. 4 is a schematic illustration for showing the producing flow for opening. The tow 21 as the material is taken out continuously and transported through an opening section where the widening means 22 using the compressed air is combined with the plural opening nip rolls 23, 24, and 25 each having the speed being increased as the line flows downstream. In this opening section, the tow 21 is widened and opened. After that, thus resultant tow is passed through the binder addition box 26 so that the binder is added to the tow (For attaining this, for example, the box is previously filled with the mist of triacetin). Finally, the assembly 20 of fibers in tows having the preferable width and density can be formed. For adding the binder to the tow, there can be listed some methods, for example, wick application system, brush application system and the like. In the wick application system, a piece of felt, into which triacetin is previously penetrated, is contacted with the surface of a roll so that the binder is transferred on the surface, and then, through which, the triacetin is added to the opened tow. On the other hand, in the brush application system, in a binder addition box provided with a slit, the binder exuded from the slit is sprayed in the form of mist to the opened tow by utilizing a rotating brush.

The assembly 20 of fibers shown in FIG. 11 can be obtained by adding uniformly the binder to the assembly 20 for the purpose of wide use. The assembly 20 of fibers shown in FIG. 12 can be obtained by adjusting the added amount of binder to the middle portion in the width direction so as to be larger than the added amount of binder to the both side portions in the width direction. The assembly 20 of fibers shown in FIG. 13 can be obtained by adjusting the added amount of binder to the both side portions so as to be larger than the added amount of binder to the middle portion. The assembly 20 of fibers shown in FIG. 14 can be obtained by leaving out the intermediate portion in the longitudinal direction in adding the binder. The assembly 20 of fibers shown in FIGS. 16, 17, 18 and 19 can be obtained by coating the binder with the brush application system and subsequently by coating the binder with the wick application system. Alternatively, the various assembly 20 of fibers shown in FIGS. 11 to 19 can be obtained by, in the binder addition box, in spraying the binder on the surface of the assembly 20 of fibers, spraying unevenly in its width direction, leaving out the intermediate portions, adjusting desirably the concentration of the binder to be coated and the like.

Particularly, in laminating the plural assembly of fibers, as stated after, as shown in FIG. 32, the belt shaped and opened assembly $A_{XO}$, of fibers and the belt shaped and opened assembly $A_{YO}$ of fibers are fed up at an angle and fed down at an angle, respectively and inserted between the two pairs of roll-roll R1-R1 and R2-R2 for their laminating. After that, the laminated assembly may be sized desirably by e.g., cutting. On the other hand, in disposing the plural assemblies $A_X$, $A_Y$, $A_Z$ of fibers separately in the width direction illustrated in FIG. 8, as shown in FIG. 33, the belt shaped assembly $A_{XO}$ of fibers composing the assembly $A_X$ of fibers, the belt shaped assembly $A_{YO}$ of fibers composing the assembly $A_Y$ of fibers and the belt shaped assembly $A_{ZO}$ of fibers composing the assembly $A_Z$ of fibers are gathered with several rollers R3 to R5. After that, the gathered assemblies of fibers may be sized desirably by e.g., cutting (Face Sheet 1)

The face sheet 1 has the character of allowing the body fluid to permeate. Accordingly, what is required for the material of the face sheet 1 is only the body fluid permeability. There can be listed as the example of the face sheet 1, a porous or non-porous non-woven fabric, a porous plastic sheet and the like. Among of these materials, as for the non-woven fabric, its material fiber is not specifically limited. There can be listed as the example of the material fiber, an olefin synthetic fiber such as polyethylene, polypropylene or the like, a polyester synthetic fiber, a polyamide synthetic fiber, a regenerated fiber such as rayon, cupra or the like, a natural fiber such as cotton or the like, and mixed fibers used in 2 or more kinds thereof. Additionally, the method for producing the non-woven fabric is not specifically limited. There can be listed as the example of the conventional methods, a spunlace method, a spunbond method, a thermalbond method, a meltblown method, a needlepunch method and the like. For example, the spunlace method is preferable when flexibility and drape characteristics are required, while the thermalbond method is preferable when bulky nature and softness are required.

The face sheet 1 may be formed with single sheet and also may be formed with laminated sheet consisting of piled plural sheets in the thickness direction.

(Wearer-Side Second Sheet 10)

In this embodiment, the face-side second sheet 10 is body fluid permeable. For example, there can be listed the same materials as those for the face sheet 1, spunlace, a pulp non-woven fabric, a mixed sheet of pulp and rayon, pointbond or crepe paper. Particularly, an airthrough non-woven fabric and a spunbond non-woven fabric are preferable.

(Body Fluid Retainable Absorbent Core AB)

The body fluid retainable absorbent core AB has the character of retaining the absorbed body fluid. Then, this core AB includes the absorbent core 4 and the covering sheet 5, which covers at least the under surface and side faces of the absorbent core 4.

(Absorbent Core 4)

As the material used for the absorbent core 4, there can be listed from the conventional materials, for example, pulp as a simple substance such as flocculated pulp, synthetic pulp or the like. The material fiber of the pulp is not specifically limited. There can be exemplified cellulose fiber from wood such as mechanical pulp, chemical pulp, dissolving pulp, or the like, artificial cellulose fiber such as rayon, acetate or the like, and so on. As wood for the cellulose fiber, acicular tree is more preferable than broad leaf tree in function and cost, because the fiber length of the acicular tree is longer than that of the broad leaf tree.

Further, as the absorbent core 4, the assembly of fibers in tows (assembly of filaments), which can be obtained by opening the tows, can be used.

In the absorbent core 4, the super absorbent polymer in the form of e.g., particles can be included. In this case, it is preferable that at least in the zone for receiving the body fluid, the super absorbent polymer is dispersed in the substantially full length of the thickness direction of the assembly of fibers composing the absorbent core 4.

If there is little or no super absorbent polymer in the upper portion, lower portion and middle portion of the assembly of fibers, such situation cannot be expressed as "dispersion situation in the substantially full length of the thickness direction". Then, as the "dispersion situation in the substantially full length of the thickness direction", the following cases can be included. First, in the assembly of fibers, the super absorbent polymer is dispersed "uniformly" in the full length of the thickness direction. Another included case is that although the super absorbent polymer is "unevenly distributed" in the upper portion, lower portion and/or middle portion, it is sure that some polymer is dispersed in the upper portion, lower portion and middle portion. Further, there are other cases not to be excluded from this dispersion situation. The one case is that some super absorbent polymer is not included in the assembly of fibers but remained on its surface. The other case is that some super absorbent polymer is passed through so as to come out from the assembly of fibers and moved onto the covering sheet 5 or moved onto the support sheet 8 as shown in FIG. 9.

(Super Absorbent Polymer)

As the super absorbent polymer particle, a particle, which is used for this kind of absorbent article, can be used as it is. Concretely, there are starch, cellulose, synthetic polymer and the like, further starch-acrylic acid (salt) graft copolymer, saponified starch-acrylonitrile copolymer, cross-linked natriumcarboxymethylcellulose, acrylic acid (salt) copolymer and the like.

The capability of the super absorbent polymer particle is not specifically limited, but the absorption is preferably 60 g/g or more. The absorption of the super absorbent polymer can be obtained in the following. First, 500.00±0.10 g of 0.9% solution of sodium chloride (prepared by dissolving 9.00 g of special great chemical sodium chloride into 991.0 g of ion exchange water) is fed into an 1 L beaker containing a rotator. Next, 2.0000±0.0002 g of sample was added to the liquid while the liquid is stirred with a magnetic stirrer. Then, the beaker is covered with Saran Wrap and the stirring is continued for one hour. Subsequently, the content of the beaker is filtered with a standard sieve (38 μm, 200 mmφ×45 mm). The gel remained on the surface of the sieve is drained with a Teflon plate and it is left for 15 minutes. Finally, the weight A of the remained gel on the surface of the sieve is measured and the absorption is obtained from the following equation.

$$C = A/S \tag{1}$$

Wherein, C is the amount (g/g) of absorbed saline, A is the weight (g) of the gel remained on the surface of the sieve, and S was the weight (g) of the sample.

As the form of super absorbent polymer particle, commonly used particulate polymer (including in the form of powder) is preferable, however the particle in another form may be used. In case of super absorbent polymer in the form of particle, its particle size is preferably 100 to 1000 μm, is more preferably, 150 to 400 μm.

The super absorbent polymer having the absorption speed of 40 sec or lower is used preferably. In case of absorption speed of higher than 40 sec, so-called reversing (the situation where the body fluid once absorbed into the absorbent core reverses outside again) would be caused easily. The absorption speed can be obtained as stated below. First, 50.00±0.01 g of 0.9% solution of sodium chloride is fed into an 100 ml beaker containing a rotator, which is, then, kept at the temperature of 25±0.2° C. in a constant-temperature water bath. Next, with a magnetic stirrer and a measuring instrument for the rotator, the solution is stirred with the rotation speed of 600±10 rpm. Then, 2.0000±0.0002 g of sample is weighed. This sample is put into the vortex in the beaker. At the same time, the measurement of the absorption speed is started with a stopwatch and each absorption speed is recorded. In this case, the absorption speed is the time (sec) taken since the sample is put into the beaker until the vortex is eliminated and the liquid level became horizontal.

The super absorbent polymer having the gel strength of 1000 Pa or higher is used preferably. The absorbent core includes the tows and becomes bulky. Then, such absorbent core can absorb the great amount of body fluid. However, after such absorption, the absorbent core will be sticky due to the great amount of body fluid. In this case, if the polymer having the above gel strength is moved into the tows, the sticky feeling can be sustained. The gel strength can be obtained as stated below. First, 20.0 g of urea, 8.0 g of sodium chloride, 0.3 g of calcium chloride, 0.8 g of magnesium sulfate, 970.9 g of ion exchange water and 0.25 g of ferrous sulfate are mixed so as to prepare totally 1 L of artificial urine (ferrous ion 50 ppm). Next, 49±0.1 g of artificial urine including 50 ppm of ferrous ion is fed into an 100 ml beaker containing a rotator. Then, the artificial urine is stirred with a magnetic stirrer. Subsequently, 1.0000±0.0002 g of sample is weighed and is put into the vortex in the beaker. After that, the content of the beaker is stirred until the vortex is eliminated and the liquid level becomes horizontal. Thus resultant gel is left for 3 hours in a box in which constant temperature (40° C.) and constant humidity (60% RH) is maintained. Then, the gel is soaked for 5 minutes in a constant-temperature water bath (25° C.). Finally, the measurement of the gel strength of the gel is performed with Neocard Meter. Conversion of unit is performed for this result through the following equation so that the gel strength (Pa) is obtained.

$$C = A \times 0.1 \tag{4}$$

Wherein C is gel strength (Pa), A is gel strength (dyne/cm$^2$) resulted from Neocard Meter and 0.1 is constant.

The basis weight of the super absorbent polymer can be desirably determined according to the absorption required for the application of the absorbent core. Therefore, although it cannot be assumed sweepingly, for example, it can be 3 to 400 g/m$^2$, preferably, it can be 50 to 350 g/m$^2$. Too small basis weight of the super absorbent polymer causes the insufficient absorbing power. On the other hand, too large basis weight of the super absorbent polymer not only brings the lightweight effect of the assembly of fibers to be cancelled but also gives the discomfort feeling due to the surplus absorbent polymer particles.

If desired, the dispersion density or dispersed amount of the super absorbent polymer can be adjusted in the direction of plane of the absorbent core 4. For example, the dispersed amount of the super absorbent polymer in the zone, into which the discharged body fluid is absorbed, can be adjusted so as to be larger than that in the other parts. Further, in taking the difference between a man and a woman into account, for men, the dispersion density (dispersed amount) is increased at the front portion, while for women, the dispersion density (dispersed amount) is increased at the intermediate portion. Additionally, zones each of which has no polymer may be localized (e.g., arranged in spots) in the direction of plane of the absorbent core 4.

Plural kinds of super absorbent polymer particles having different particle-size are prepared so that they can be added by turn in the direction of thickness of the article. For example, plural super absorbent polymer particle dispersing means are placed along the line so as to be spaced one another. Then, the super absorbent polymer particles having each kind of particle size are fed into each dispersing means so that these means are arranged in the order of increasing size. In this way, the polymer can be distributed in the order of increasing particle size. Thus, in the absorbent core 4, the smaller size particles are supplied in the lower portion while the larger size particles are supplied in the upper portion.

The absorptive property is determined depending on the proportion of the super absorbent polymer particles with respect to the assembly of fibers. In the absorbent core 4, in the plane area of 5 cm×5 cm in the zone, into which the body fluid is directly discharged, the weight proportion; the super absorbent polymer particle/the assembly of fibers is preferably 1 to 14, more preferably 3 to 9.

(Size and Weight of Absorbent Core)

As for the size of absorbent core 4, it has preferably the planar projection area of 400 cm$^2$ or more and the thickness of 1 to 10 mm, more preferably 1 to 5 mm. The absorbent core 4 having the size in this range gives the remarkable advantage in improving the resilience without increase of weight, thickness and cost. Further, the absorbent core 4 is preferably adapted to have the mass of 25 g or less, more preferably 10 to 20 g. The absorbent core 4 having the mass in this range gives the remarkable advantage in that there is no need of member for exclusive use.

(Compressive Property of Absorbent Core)

It is preferable than the absorbent core 4 has the compressive resilience RC of 40 to 60%, more preferably 50 to 60%. In this way, sufficient resiliency can be obtained by the absorbent core 4 solely.

Further, it is preferable that the absorbent core 4 has the work of compression WC of 4.0 to 10.0 gf·cm/cm$^2$, because such absorbent core 4 can be compressed to be compact to the same degree as or higher degree than the conventional absorbent cores, in packing the article for the market.

The compressive property can be adjusted by controlling the fiber density of the assembly of fibers through the opening and the like; by selecting the type of fiber material, the type of binder e.g., plasticizer or the process level of binder treatment, and the combination thereof.

The definition of the work of compression (WC) is the energy consumption caused by pressing the center of a specimen (the absorbent core) of 200 mm long by 50 mm wide to 50 gf/cm$^2$. This work of compression can be measured with Handy-Type Compression Tester (KES-G5:KATO TECH CO., LTD.). The measuring conditions are in the following. SENS: 2, Type of Force Sensor: 1 kg, SPEED RANGE: STD, DEF Sensitivity: 20, Pressurization Area: 2 cm$^2$, Sampling Rate: 0.1 (Standard), STROKE SET: 5.0, Maximum Weighting: 50 gf/cm$^2$.

On the other hand, the compressive resilience (RX) is a parameter regard to the resiliency of compressed fiber. Accordingly, the higher the resiliency is, the larger the compressive resilience is. This compressive resilience can be measured with Handy-Type Compression Tester (KES-G5: KATO TECH CO., LTD.). The measuring conditions are the same as those in the above work of compression.

(Covering Sheet)

As the covering sheet 5, there can be used tissue paper, particularly crepe paper, a non-woven fabric, a polyethylene laminated non-woven fabric, a perforated sheet and the like. However, it is preferable that the super absorbent polymer particle can be prevented from going through the covering sheet. When the non-woven fabric is used instead of the crepe paper, a hydrophilic SMMS (spunbond/meltblown/meltblown/spunbond) non-woven fabric is specifically preferable. This non-woven fabric may be fabricated from polypropylene, polyethylene/polypropylene, and the like. The basis weight of this covering sheet is preferably 8 to 20 g/m$^2$, more preferably 10 to 15 g/m$^2$.

As shown in FIGS. 2 and 9, the covering sheet 5 may cover the whole of the absorbent core 4. Alternatively, as shown in FIG. 10, the covering sheet 5 may cover only the under surface and the side faces of the absorbent core 4. Further, it may be possible although not shown, that the absorbent core 4 is covered only at its top face and its side faces with crepe paper or a non-woven fabric and at its bottom face with a body fluid impermeable sheet such as a polyethylene sheet or the like, and that the absorbent core 4 is covered at its top face with crepe paper or a non-woven fabric and at its side faces and its under surface with a body fluid impermeable sheet such as a polyethylene sheet or the like (the covering sheet comprises these materials as the components). Then, if desired, it is possible that the covering sheet 5 is defined by an upper layer and a lower layer and the layer of the absorbent core 4 is interposed between these two layers and that the covering sheet 5 is defined by a single sheet disposed only at the under surface of the absorbent core 4. However, these embodiments are not preferable, because the covering sheets in these embodiments cannot prevent the removal of the super absorbent polymer.

(Support Sheet)

If desired, in such case as the super absorbent polymer is included in the absorbent core 4, the support sheet 8 may be disposed at the under surface-side of the absorbent core 4, e.g., as shown in FIGS. 9 and 10, the support sheet 8 may be interposed between the absorbent core 4 and the wearer-side surface of covering sheet 5 (the portion below the absorbent core 4).

Thus the super absorbent polymer may be interposed between the support sheet 8 and the absorbent core 4. In producing step of the absorbent core, in the subsequent steps, or in the marketing channel to each consumer, it sometimes occurs that the super absorbent polymer removed from the absorbent core 4. In such case, the removed polymer causes roughness, which brings discomfort to each consumer, when he or she touches the article in use. This is the reason why the support sheet 8, which has the capability of retaining the super absorbent polymer, is disposed between the absorbent core 4 and the covering sheet 5. Precisely, since the toughness supplied only by the covering sheet 5, which is fabricated from tissue paper (crepe paper) and the like, is not enough to retain the super absorbent polymer, the support sheet 8 reinforces the toughness. As a result, the discomfort caused by this roughness when the consumer touches the article in use, can be reduced or eliminated by the support sheet 8.

FIG. 9 shows conceptually that the super absorbent polymer particles 9 are provided below the absorbent core 4 or that the super absorbent polymer particles 9, which are included in the absorbent core 4, are then removed from the absorbent core 4 during the producing steps or in the marketing channel to each consumer so as to be collected on the support sheet 8.

The material of the support sheet 8 is not specifically limited and what is required for it is supporting ability for the absorbent polymer. There can be concretely listed, for example, a non-woven fabric, crimped pulp, a low absorbent cotton fiber (e.g., an un-degreased cotton fiber, a degreased cotton fiber, a treated rayon fiber with water repellant agent or hydrophobizing agent or the like), a polyethylene fiber, a polyester fiber, an acrylic fiber, a polypropylene fiber, silk, cotton, hemp, nylon, a polyurethane fiber, an acetate fiber and the like.

When the non-woven fabric is used as the support sheet 8, it is preferable that the non-woven fabric has the work of compression of 0.01 to 10.00 gf·cm/cm$^2$, more preferably 0.01 to 1.00 gf·cm/cm$^2$ and the compressive resilience of 10 to 100%, more preferably 70 to 100% based on KES test.

As stated before, the reason why the support sheet 8 is disposed is to support the super absorbent polymer, which is fallen downwardly (removed) from the absorbent core 4. Therefore, even if the super absorbent polymer is removed, the wearer contacts them not directly but through the covering sheet 5 and the support sheet 8. Thus, there is no fear of discomfort feeling for the wearer. Particularly, if the support sheet is fabricated from the non-woven fabric having the above work of compression and the above compressive resilience, such support sheet fulfills sufficiently its own function.

Further, the existed super absorbent polymer is remained by the support sheet 8 so that the polymer does not move on the covering sheet 8. Accordingly, there is no fear to generate unevenly distribution of absorption capability. Particularly, in order to prevent the super absorbent polymer from moving on the support sheet 8, for example, hot melt adhesive having the adhesion can be previously coated on the support sheet 8. Alternatively, the upper surface (the wearer-side surface) of the support sheet 8 may be processed into a rough face to prevent the super absorbent polymer from moving on the support sheet 8. As means for making surface rough or for carding for this purpose, there can be listed the use of non-net face which is a reverse face touching a net in production of non-woven fabric, a marble treatment, processing by needle punch and brushing treatment and the like.

As shown in FIG. 10, the support sheet 8 may be disposed only below the absorbent core 4. Then, as shown in FIG. 9, the support sheet 8 also may be extended to pass along the side faces of the absorbent core 4 and continuously along the upper surface of the absorbent core 4. Further, plural support sheets 8 can be used while they are piled.

In the above embodiments shown in FIGS. 9 and 10, the support sheet 8 is interposed between the absorbent core 4 and the wearer-side of the covering sheet 5. However, the support sheet 8 can be disposed at the undersurface-side (not shown) with respect to the covering sheet 5. What is necessary is only that the support sheet 8 is disposed at the undersurface-side with respect to the absorbent core 4. Such configuration decreases or eliminates the discomfort feeling of the consumer when he or she touches the undersurface of the article.

(Back Sheet 2)

In this embodiment, the back sheet is body fluid impermeable. Accordingly, what is required for the material of the back sheet is this fluid impermeability. Concretely, there can be listed, for example, olefin resin such as polyethylene resin, polypropylene resin, or the like, a laminated non-woven fabric formed by a laminating non-woven fabric on a polyethylene sheet or the like, a substantially impermeable non-woven fabric, whose impermeability is caused by combined waterproof film (in this case, the body fluid impermeable sheet is formed by combining the waterproof film with the non-woven fabric) and the like. It is needless to say that other than these materials, there can be listed liquid impervious but moisture permeable material, which is often used in these days because of its resistance to stuffy feeling. As this liquid impervious but moisture permeable material, for example, slightly porous sheet can be listed. This is produced in the following way. First, inorganic filler is kneaded with olefin resin such as polyethylene resin, polypropylene resin, or the like so as to mold a sheet. Then, this sheet is subjected to uniaxial drawing or biaxial drawing so that the slightly porous sheet can be obtained.

(Relation Between Face Sheet 1 and Face-Side Second Sheet 10)

It is preferable that the face sheet 1 has the basis weight of 8 to 40 g/m$^2$ and the thickness of 0.2 to 1.5 mm and the face-side second sheet 10 has the basis weight of 15 to 80 g/m$^2$ and the thickness of 0.2 to 3.5 mm. Under such conditions, the embossing can be carried out sufficiently, without inhibiting the permeability.

The face-side second sheet 10 may be disposed with full length of the longitudinal direction of the article. Further, the body fluid permeable member 20 may be disposed with full length of the longitudinal direction of the article. In addition, in the both of the face-side second sheet 10 and the body fluid permeable member 20, plural sheets 10 and plural members 20 may be respectively, disposed so as to space in the longitudinal direction of the article and in the width direction of the article (That is to say, they are disposed intermittently).

(Relation Between Face-Side Second Sheet 10 and Permeable Member 20)

As for the positional relation between the face-side second sheet 10 and the permeable member 20, on the plan view, they should be superimposed at least partly. Then, it is preferable that the area of the face-side second sheet 10 covers 70% or more of the whole area of top face of the body fluid permeable member 20.

(Relation Between Permeable Member 20 and Absorbent Core 4)

The positional relation between the permeable member 20 and the absorbent core 4 can be determined desirably in design according to the actual application. Precisely, the positional relation is determined according to, for example, configuration of each absorbent article comprising the permeable member 20 and the absorbent core 4. Such embodiments are shown in FIGS. 21 to 24. In every embodiment, the permeable member 20 and the absorbent core 4, which is laminated on the under surface of the permeable member 20, are included. For example, when the permeable member 20 and absorbent core 4 are used for an absorbent article such as a sanitary napkin or the like, the surface of the permeable member 20, on which the assembly of fibers are exposed, is to be the wearer-side surface (being closer to the wearer's excretory organ). In this way, the discharged body fluid such as menstrual blood or the like can be absorbed into the permeable member 20 quickly and adapted to reach the absorbent core 4, where the body fluid is retained and saved. As explained here, the quick absorbing and retaining of the body fluid can be ensured in the permeable member 20. Further, since the binder is added to cause fiber-fiber bonding, the body fluid can be absorbed into the permeable member 20 repeatedly one after another. Hence, the body fluid such as menstrual blood is not remained on the external surface of the article, which means that there is no fear of unclear feeling for the wearer. Moreover, in this article, the body fluid permeability is not decreased near the wearer-surface, resulting in high protection against the leakage.

On the plan view seen from the wearer-side, the permeable member 20 may be configured preferably as stated below. First, as shown in FIG. 22, the permeable member 20 is disposed at the middle portion of the absorbent core 4 in its width direction so as to extend along the longitudinal direction. Next, as shown in FIG. 23, the permeable member 20 is disposed only on the small zone corresponding to the wearer's excretory organ. Then, as shown in FIG. 24, the permeable member 20 is wide at its front portion while it is narrow at its back portion. Alternatively, an absorbent core 4 is incorporated into a sanitary napkin so that the longitudinal direction of the absorbent core 4 corresponds to the longitudinal direction of the sanitary napkin. In this sanitary napkin, the assembly of fibers can be easily adapted to locate in only the zone near the wearer's excretory organ. Accordingly, the inexpensive material can be used for the rest of the absorbent article, which contributes to the low producing cost.

As stated above, the permeable member 20 and the absorbent core 4 are laminated in several manners. Then, as shown in FIGS. 25 to 30, embossing can be carried out on at least one of the permeable member 20 and the absorbent core 4. The method for embossing is not specifically limited, actually, if the embossing is carried out on the permeable member 20, there is fear that the body fluid permeability of the permeable member 20 is lowered due to the pressing. Accordingly, it is preferable that embossing e is applied not on the permeable member 20 but on the wearer-side surface of the absorbent core 4. It is more preferable that the absorbent core 4, which is disposed on the under surface of the permeable member 20, is formed so as to be larger than the permeable member 20 in the width and length, and then, the embossing is applied preferably to the wearer-side exposed surface (on which, the permeable member 20 is not superposed,) of the absorbent core 4.

The preferable embodiments of the embossing will be stated in the following. First, as shown in FIG. 25, the absorbent core 4 is disposed on the under surface of the permeable member 20, which is disposed at only the restricted small area. Then, the embossing e is applied on the absorbent core 4 along its width direction in the form of line at the front-side and the back-side with respect to the permeable member 20 respectively. Next, as shown in FIG. 26, the absorbent core 4 is disposed on the under surface of the permeable member 20, which is disposed at only the restricted small area. Then, the embossing e is applied on the absorbent core 4 along its longitudinal direction in the form of plural number of lines at the front-side and back-side with respect to the absorbent member 53B. Subsequently, as shown in FIG. 27, the absorbent core 4 is disposed on the under surface of the permeable member 20, which is disposed on the absorbent core 4 so as to extend along its longitudinal direction at the middle portion in the width direction. Then, the embossing e is applied on the absorbent core 4 in its longitudinal direction in the form of line at the right side and left side with respect to the permeable member 20. Finally, as shown in FIG. 28, the absorbent core 4 is disposed on the under surface of the permeable member 20, which is disposed on the absorbent core 4 so as to extend along its longitudinal direction at the middle portion in the width direction. Then, the embossing e is applied on the absorbent core 4 in the form of line descending vertically from the front end to the intermediate portion and continuously descending outwardly at the right side and left-side with respect to the permeable member 20.

Thus embossed absorbent core 4 and the permeable member 20 are incorporated into e.g., a sanitary napkin so that the longitudinal direction of the absorbent core 4 and the permeable member 20 corresponds to the longitudinal direction of the sanitary napkin. In this way, the permeable member 20 can be easily located at the zone near the wearer's excretory organ, for example, the zone into which discharged menstrual blood is absorbed, and besides, the body fluid discharged to the permeable member 20 can be diffused along the embossing e. Consequently, this absorbent article offers sufficient protection against the side leakage.

Further, in incorporating the permeable member 20 and the absorbent core 4 into an absorbent article, a body fluid permeable sheet, so called second sheet may be interposed between the permeable member 20 as well as the absorbent core 4 and body fluid permeable top sheet 1. In this case, embossing e can be applied integrally to the second sheet and at least one of the permeable member 20 and the absorbent core 4. For example, as shown in FIGS. 29 and 30, in each embodiment, it is preferable that the wearer-side surface of the permeable member 20, which is disposed at only the small zone, is covered by the second sheet S, and embossing e is applied to the second sheet S and the absorbent core 4 integrally so that the embossing e surrounds the absorbent core 4 in the form of square. In each embodiment, by integrating surely the second sheet S and the absorbent core 4, the resultant absorbent article can fulfill effectively the protective function against the side leakage due to the embossing as well as the preventive function against the reversing of the body fluid on account of the second sheet.

In the embodiments shown in the plan views of FIGS. 21 to 30, the absorbent core 4 is laminated on the under surface of the permeable member 20 and the binder is added uniformly to the whole surface of the permeable member 20. However, the binder can be added in the same manner as shown in FIGS. 11 to 19 to the permeable member 20 laminated by the absorbent core 4. For example, as shown in FIG. 31, the adhesion degree or fusion degree of the fibers in their contacting portions in the form of line or dot at the middle portion in the width direction is stronger than those at the both side portions in the width direction by adjusting the added amount of binder to the middle portion so as to be larger than the added amount of binder to the both side portions. Thus, it can be said that the permeable member 20 holds, at its undersurface, the thickness of the absorbent core 4.

In such laminating configuration formed by the permeable member 20 and the absorbent core 4, by using the material for the absorbent core 4 so that the decrease in its thickness of this material is lower than the decrease in the thickness of the permeable member 20, since the absorbent core 4 is laminated on the under surface of the permeable member 20, the decrease in the thickness of the permeable member 20 can be complemented by the absorbent core 4. As a result, in this laminating configuration, the stiffness can be kept not only when the body fluid permeates but also under the pressure. The dimension of decrease in thickness can be expressed by work of compression (WC). It is preferable that the work of compression (WC) of the absorbent core 4 is preferably 1.0 to 3.0 gf·cm/cm$^2$, while the work of compression (WC) of the permeable member 20 is preferably 3.0 to 10.0 gf·cm/cm$^2$. These values can be attained by, for example, using the permeable member 20 having the density of 10 to 100 kg/m$^3$ and the absorbent core 4 having the density of 10 to 100 kg/m$^3$. If the work of compression (WC) is low, under and after the application of pressure, the dimension of decrease in thickness is low and the stiffness is offered. On the other hand, if the work of compression (WC) is high, under and after the application of pressure, the dimension of decrease in thickness is high and the stiffness is easily lost. The work of compression (WC) can be measured, for example with Handy-Type Compression Tester (KES-G5:KATO TECH CO., LTD.). Concretely, it can be measured with this tester, specimen size and shape: 200 mm long×50 mm wide and square, measured position: the center of the specimen of 200 mm long×50 mm wide, measuring conditions: SENS: 2, Type of Force Sensor: 1 kg, SPEED RANGE: 0.1, DEF Sensitivity: 20, Pressurization Area: 2 cm$^2$, Sampling Rate: 0.1 (Standard), STROKE SET: 5.0, Maximum Weighting: 50 gf/cm$^2$.

(Other Embodiments of Permeable Member 20)

It is possible that the plural layers are laminated in the body fluid permeable member 20, with only essential parts shown in FIGS. 5 to 8. In these drawings, each permeable member 20 comprises the laminated two layers, the upper layer 20A and the lower layer 20B. Then, there are some embodiments, in the first case, the width of the upper layer 20A is the same as that of the lower layer 20B (FIG. 5), in the next case, the width of the upper layer 20A is smaller than that of the lower layer 20B (FIG. 6), and the third case, the width of the upper layer 20A is larger than that of the lower layer 20B (FIG. 7).

As shown in FIG. 8, the plural permeable members 20A, 20B are disposed separately side by side in the direction of plane such as width direction.

In such configuration where the plural permeable members 20A and 20B are disposed, besides the width of the permeable member, the added amount of binder, density, bulk, denier of fiber in the preamble member and the like can be designed desirably so that they are different between those of the permeable members 20A, 20B, respectively. For example, the larger amount of binder may be added to the permeable members 20B located at opposite side portions in the width direction for stronger fiber bonding, while the smaller amount of binder may be added to the permeable member 20A located at the middle portion in the width direction for weaker fiber bonding.

(Embodiment of Producing Method of Absorbent Article)

Now, the producing method of absorbent article will be exemplified by way of embodiments of sanitary napkins. The first embodiment of sanitary napkin $N_1$ is shown in FIGS. 34 and 35. In the first embodiment of sanitary napkin $N_1$, as shown in FIG. 34, both of the absorbent core 4 and the permeable member 20A are extended longitudinally without reaching the front end and the back end of the sanitary napkin. Then, as shown in FIG. 35, the absorbent core 4 and the permeable member 20 are laminated and at the same time, the permeable member 20 is disposed on the wearer-side.

The producing method of the sanitary napkin $N_1$ of this embodiment is shown in FIG. 36. First, adhesive G is coated on the suitable portions of the wearer-side surface of the belt shaped absorbent material $4_C$, which is fabricated from e.g., airformed pulp and which is fed downwardly with e.g., belt conveyor. Next, the belt shaped assembly $20_C$ of fibers (This will be the permeable member 20A), to which binder is previously added, is continuously laminated and adhered to the absorbent material $4_C$. Then, the resultant belt shaped and laminated structure $X_C$ is sized desirably with the cutters 100, 100 to be individual structures X, X . . . , which are further fed downwardly. After that, these individual structures X, X . . . are fed downwardly with e.g., belt conveyor while the belt shaped top sheet material $110_C$ (in order to form this top sheet material $110_C$, the face sheet 1 and the face-side second sheet 10 are previously laminated so that embossing is carried out on these laminated sheets) is superimposed on the upper surfaces (the wearer-side faces) of the structures X, X . . . and the belt shaped back sheet material $2_C$ is superposed on the under surfaces of the structures X, X . . . . Subsequently, the belt shaped top sheet material $110_C$ and the belt shaped back sheet material $2_C$ are adhered with the heat sealers 111, 111 at the adhesion points H, which are spaced desirably. Finally, these structures are cut at these adhesion points H, thus each absorbent article can be obtained separately. Each adhesion point H defines the end of the sanitary napkin in its longitudinal direction.

FIGS. 37 and 38 show the second embodiment of the sanitary napkin $N_2$. As shown in FIG. 37, in the sanitary napkin $N_2$ of the second embodiment, the absorbent core 4 is extended longitudinally without reaching the front end and the back end of the sanitary napkin, while the permeable member 20A is extended longitudinally so as to reach these both ends. Further, as shown in FIG. 38, the absorbent core 4 and the permeable member 20A are laminated and at the same time, the permeable member 20A is disposed on the wearer-side.

The producing method of the sanitary napkin $N_2$ of this embodiment is shown in FIG. 39. First, the belt shaped absorbent material $4_C$, which is fed downwardly with e.g., belt conveyor, is sized desirably with the cutters 100, 100 to be the absorbent cores 4, 4 . . . , which are further fed downwardly. Next, adhesive G is coated on the suitable portions of the wearer-side surface of each absorbent core 4, 4 . . . . Then, the belt shaped assembly $20_C$ of fibers (This will be the permeable member 20A), to which binder is previously added, is continuously laminated and adhered to the cores 4, 4 . . . . Also during such lamination, the resultant belt shaped and laminated structure $X_C$ is further fed downwardly. After that, the belt shaped top sheet material $110_C$ is superimposed on the upper surface (the wearer-side surface) of the structure $X_C$ and the belt shaped back sheet material $2_C$ is superposed on the under surface of the structure $X_C$. Subsequently, the belt shaped top sheet material $110_C$ and the belt shaped back sheet material $2_C$ are adhered with the heat sealers 111, 111 at the adhesion points H, which are spaced desirably. Finally, these absorbent structures adhered by the face sheet and the back sheet are cut at these adhesion points H, thus each sanitary napkin $N_2$ can be obtained separately.

FIGS. 40 and 41 shows the third embodiment of the sanitary napkin $N_3$. As shown in FIG. 40, in the sanitary napkin $N_3$ of the third embodiment, the absorbent core 4 is extended longitudinally without reaching the front end and the back end of the sanitary napkin $N_3$, while the permeable member 20A is disposed at the restricted small central portion of the absorbent core 4. Further as shown in FIG. 41, the permeable member 20A, which is wrapped with the covering sheet C, is laminated and disposed on the wearer-side surface of the absorbent core 4.

As for the sanitary napkin $N_3$ of the third embodiment, the essential part of its producing method is shown in FIG. 42. First, adhesive G is coated on the suitable portions of the wearer-side surface of the belt shaped covering sheet $C_C$, which is fed downwardly. Next, the belt shaped assembly $20_C$ of fibers, to which binder is previously added and whose width is smaller than the width of the covering sheet $C_C$, is continuously superimposed and adhered to the wearer-side surface of the covering sheet $C_C$. During this, the resultant belt shaped and laminated structure C is further fed downwardly. Then, with the folding member 112, longitudinal opposite side portions of the covering sheet Cc are folded around the side edges of the belt shaped assembly $20_C$ of fibers so as to cover the wearer-side surface of the assembly $20_C$ of fibers resulting in the belt shaped assembly $20_C$ of fibers wrapped with the covering sheet Cc. After that, this is sized desirably to plural permeable members 20. Although not shown in the drawings, the permeable members 20A, wrapped with the covering sheets C, respectively, are processed as follows. Each permeable member is disposed on the wearer-side surface of each absorbent core 4 having the suitable size. Alternatively, each permeable member is disposed on the wearer-side surface of the belt shaped absorbent material $4_C$ followed by cutting. After that, in the both cases, individual laminated structures X can be obtained. Subsequently, the laminated structures X are fed downwardly, while the belt shaped top sheet material $110_C$ is superimposed on the top (the wearer-side) surfaces of the laminated structures X and the belt shaped back sheet material $2_C$ is superimposed on their under surfaces. Thus, the belt shaped top sheet material $110_C$ and the belt shaped back sheet material $2_C$ are adhered with the heat sealers 111 at the adhesion points H, which are spaced desirably. Finally, this is cut at these adhesion points H and the individual sanitary napkin $N_3$ can be obtained separately.

[Embodiment of Absorbent Pad]

Now, the embodiment of disposable absorbent pad, which is used for applying the wearer-side surface of a pants-type diaper for adults will be explained. The absorbent pad shown FIGS. 43 and 44 comprises the face sheet 11, which is permeable for discharged body fluid and which is faced with the wearer's skin, the permeable member 20, which is discharged body fluid permeable, and the absorbent element AB, which is disposed on the under surface of the permeable member and which retains the discharged body fluid, in this order from the wearer-side surface to the under side surface. Further, the absorbent pad comprises the barrier cuffs 30, 30.

(Face Sheet 11)

In the face sheet 11, through holes 11H, 11H . . . for the discharged body fluid are formed at least in the zone corresponding to the wearer's anus. In this embodiment, many through holes 11H, 11H . . . are formed on the whole of the face sheet 11. As the preferable group of the through holes formed at least in the zone corresponding to the wearer's anus, the effective open area of the single through hole is 3 to 75 mm², and the open area ratio is 10 to 80%. If the open area and open area ratio are small, the permeability for the solid component of the soft feces is lowered. Commonly, after the soft feces are passed through the through holes, the solid component of the soft feces is remained on the surface of the permeable member 20. In this situation, if the open area is too large, the remained solid component is brought into contact with the wearer's skin, which causes skin irritation or requires troublesome cleaning treatments. Further, if the open area ratio is too large, the mechanical strength of this face sheet 11 is undesirably decreased.

As the material of the face sheet 11, a non-woven fabric preferably enables good touch for the wearer, plastic sheet also can be used. The through hole 11H has the open shape of, besides the circle shown in the drawing, ellipse, triangle, rectangle, rhombus, hexagon and the like. Many through holes 11H are arranged regularly or irregularly. As the preferable non-woven fabric, there can be used an airthrough non-woven fabric, resin bonded non-woven fabric, an air laid non-woven fabric, a spunlaced non-woven fabric, a heat roll treated non-woven fabric, a spunbond fabric and so on. If the fineness of the fiber forming the non-woven fabric is 2 to 15 dtex, preferably 3 to 10 dtex, more preferably 4 to 10 dtex, which ensures the space for absorbing the soft feces and improves the permeability of the face sheet. The basis weight of the face sheet is preferably 5 to 45 g/m².

As shown in FIG. 48, if desired, the face sheet 11 can be omitted.

As stated in the above explanation about the sanitary napkin, embossing can be carried out integrally on the face sheet 11 and the face-side second sheet, which is superposed on the under surface of the face sheet 11. However, there is no drawing of its configuration, because this configuration is the same as that explained in the case of sanitary napkin.

(Barrier Cuffs)

At the opposite side portions of the face sheet 11, barrier sheets 6 are disposed so that their front end-side portion and the back end-side portion in the longitudinal direction are fixed on the face sheet 11. Then, the opposite side portions of the intermediate free portions are folded back inwardly. Further, elastically expansible members 32 such as rubber strands or the like are fixed in the elongated state on the opposite side portions. Thus, the barrier sheets define barrier cuffs 30, 30, whose free portions are standing in wearing. The barrier cuffs are not essential, but are provided preferably for the protection against the side leakage of soft feces.

(Permeable Member 20)

The permeable member 20, which is faced directly with the undersurface of the face sheet 11, is basically the same as that explained in case of sanitary napkin. Precisely, as the permeable member 20, the assembly of fibers, for example, a sheet obtained by opening filaments in tows can be used. A sheet composed mainly by water-repellent fibers or hydrophobic fibers is more preferable. As the preferable water-repellent filament or hydrophobic filament, a PET fiber, a PP fiber, a PE fiber or the like, and besides, a core-in-sheath type filament using at least one of these fibers can be used preferably.

If the permeable member 20 is hydrophilic, the member is suitable for urine due to high permeability. However, for example, when soft feces reach the permeable member 20 as the discharged body fluid, the solid component of the soft feces is retained between the fibers. This situation causes the retention of also the liquid component of the soft feces and the liquid component included in the solid component. That is to say, the both of solid component and liquid component of the soft feces are retained and remained in the permeable member 20, thus, they cannot be moved to the absorbent element AB smoothly. Contrary to this, when the permeable member is composed of mainly the water-repellent or hydrophobic fibers, even if most of solid component of the soft feces is retained between fiber-fiber, the liquid component of the soft feces and the liquid component included in the solid component can be filtered due to the function of the water-repellent or hydrophobic fibers. Thus, the liquid component of the soft feces is separated from the solid component and moved into the absorbent element AB. In this way, the permeable member 20 has enough capability to receive coming soft feces and continuously fulfils filter function. As a result, the large amount of liquid component of the soft feces can be moved rapidly to the absorbent element AB.

It is preferable that the filaments of the permeable member 20 are arranged in the direction of sheet-plane of the article. Such configuration improves the permeability for soft feces, particularly for the liquid component of the soft feces. The reason will be stated below. In a non-woven fabric comprised by irregularly arranged short fibers, its fiber density is high and possibility of decreasing the fiber density is limited because of maintained mechanical strength. Accordingly, the solid component of the soft feces cannot be moved smoothly into the permeable member 20. Contrary to this, if the non-woven fabric is composed of assembly not of short fibers but of filaments, the solid component of the soft feces can be moved smoothly into the filaments. Further, if the filaments of the permeable member 20 are arranged in the direction of the thickness of the article, unless both of the solid component and the liquid component of the soft feces are passed between the filaments, the liquid component cannot be moved into the absorbent element AB smoothly. However, if the filaments are arranged in the direction of sheet-plane, the solid component of the soft feces is retained and remained between the filaments. In this situation, since the filament group fulfils the filter function, the large amount of liquid component of the soft feces is moved rapidly into the absorbent element AB.

When the filaments of the permeable member 20 are arranged in the direction of sheet-plane, it is possible that as shown in FIG. 49(*a*), the filaments are arranged in the longitudinal direction of the article and it is also possible that as shown in FIG. 49(*b*), they are arranged in the width direction. However, the liquid component of the soft feces can permeate more efficiently through the arranged filaments in the longitudinal direction than through the arranged filaments in the width direction, because the liquid component can be diffused rapidly back and forth in the arranged filaments in the longitudinal direction.

In the permeable member 20, it is preferable that spiral crimp is applied to the filaments. By doing so, these filaments fulfill the filter function more effectively so that larger amount of liquid component of the soft feces can be moved rapidly into the absorbent element AB.

Further, as the assembly of filaments, its fiber density is, under the thickness of 10 mm, preferably 0.075 g/cm³ or less, is more preferably 0.0060 to 0.0070 g/cm³. The fiber density of the assembly of filaments can be adjusted by the opening degree of the tows. Too high fiber density eliminates the advantage of the assembly of fibers in tows and the permeability of the liquid component of the soft feces is decreased.

The basis weight of the permeable member 20 is preferably 10 to 100 g/m². The basis weight of the permeable member can be adjusted by the selection of the tows as the material or the manufacturing conditions.

(Absorbent Element AB)

The absorbent element AB, which is faced directly with the permeable member 20, comprises the absorbent core 4, which retains the discharged body fluid, and the surface layer covering sheet 5A, which is disposed between the absorbent core 4 and the permeable member 20.

(Absorbent Core 4)

As the material of the absorbent core 4, there can be used flocculent pulp, an airformed composite of fiber other than the pulp, and an assembly of fibers (an assembly of filaments) formed by opening the tows as stated in the explanation of the sanitary napkin. Here, the flocculent pulp is produced by confounding treatment, with air stream or water stream, of an airformed composite, which is formed by the conventional methods from cellulose fiber from wood such as chemical pulp, dissolving pulp, or the like, artificial cellulose fiber such as rayon, acetate or the like, and so on. (As wood for the cellulose fiber, acicular tree is more preferable than broad leaf tree in function and cost, because the fiber length of the acicular tree is longer than that of the broad leaf tree.)

As shown in FIG. 46, instead of the single layer, the absorbent core 4 may comprise the upper absorbent core 4A having the smaller width and the lower absorbent core 4B having the larger width.

(Super Absorbent Polymer)

At the preferable portion below the surface layer covering sheet 5A of the absorbent element AB, super absorbent polymer (SAP) particles can be provided in order to retain the large amount of liquid component. They are dispersed to scatter on the absorbent core 4. Alternatively, they are dispersed in the absorbent core 4.

As the preferably used super absorbent polymer, there can be listed carboxymethylcellulose, poly (acrylic acid) and its salts, cross-linked poly (acrylic acid)salt, starch-acrylic acid graft copolymer, hydrolyzed starch-acrylonitrile graft copolymer, cross-linked polyoxyethylene, cross-linked carboxymethylcellulose, partly cross-linked water swelling polymer such as polyethylene oxide, polyacrylamide or the like, isobutylene-maleic acid copolymer and the like. Anti-blocking agent may be added to the super absorbent polymer in order to inhibit the blocking caused by the absorption of moisture. As the form of the super absorbent polymer, there can be listed powder, particle, granulated powder, pellet, sol, suspension, gel, film, and non-woven fabric. Among of them, everything is possible, particularly super absorbent polymer in the form of particle is used preferably.

There can be listed some methods adopted for taking the super absorbent polymers into the absorbent core. For example, in one method, the super absorbent polymer in the form of particles is dispersed to the absorbent core 4. In another method, monomer (which is to be the super absorbent polymer) is soaked into the absorbent core 4, and after that, this monomer is polymerized. Then, in still another method, the super absorbent polymer in the form of gel, which is not cross-linked yet, is coated on the absorbent core 4 and after that, the polymer is cross-linked. The basis weight of the super absorbent polymer can be desirably determined according to the absorption required for the application of the absorbent core 4. Therefore, although it cannot be assumed sweepingly, it can be generally 0.03 $g/cm^2$ or less, and it is more preferably 0.01 to 0.025 $g/cm^2$.

Instead of taking the super absorbent polymer into the absorbent core 4, the super absorbent polymer layer may be disposed on at least one of the wearer-side surface and the under surface of the absorbent core 4. Specifically the super absorbent polymer layer may be disposed on the under surface of the absorbent core 4. In these cases, the super absorbent polymer can be adhered with adhesive to the sheet covering the absorbent core 4. As the adhesive, the above thermoplastic resin can be used.

Further, as shown in FIG. 46, when the absorbent core is composed of two layers; the upper absorbent core 4A and the lower absorbent core 4B, the super absorbent polymer particles are taken into only the lower absorbent core 4B. In the drawing, the super absorbent polymer particle is designated by the reference symbol ○.

(Covering Sheet 5)

The external surface of the absorbent core 4 is partly covered with the surface layer covering sheet 5A and the rest of the external surface of the absorbent core 4 is covered with another covering sheet 5C. That is to say, the covering sheet 5 for the absorbent core 4 is composed of the covering sheet 5A and the covering sheet 5B.

The surface layer covering sheet 5A may be, as shown in FIG. 47, perforated sheet. In this case, it is preferable from the viewpoint of liquid component permeability that the effective open area of the single through hole is 0.5 to 40 $mm^2$, and the open area ratio is 1 to 80%. When the covering sheet 5A is a perforated sheet, various kinds of non-woven fabrics may be used and perforated. Alternatively, plastic sheets can be used and perforated.

As the surface layer covering sheet 5A, there can be used an airthrough non-woven fabric, a resin bonded non-woven fabric, an air laid non-woven fabric, a spunlaced non-woven fabric, a heat roll treated non-woven fabric, a spunbond non-woven fabric and so on. Among of them, specifically the airthrough non-woven fabric is preferable. Further, in using the airthrough non-woven fabric, a water-repellent fiber or a hydrophobic fiber is used more preferably. As the preferable water-repellent fiber or hydrophobic fiber, a PET fiber, a PP fiber, a PE fiber or the like, and besides, a core-in-sheath type fiber using these fibers can be used preferably.

Generally, for the purpose of keeping the shape of the absorbent core 4 and the like, the absorbent core 4 is to be covered with crepe paper or the like. However, the liquid component of the soft feces is different from the urine in the viscosity. Precisely, in this absorbent pad, it may be occurred that the permeability is decreased due to the material of the covering sheet. If the liquid component of the soft feces cannot permeate smoothly from the wearer-side surface of the absorbent core 4, when the liquid component of the soft feces discharged from the permeable member 20 intends to move into the absorbent core 4, its wearer-side surface turns to block such moving as an barrier. As a result, for the soft feces, it is difficult to permeate through the permeable member 20. On the contrary, in case that the airthrough non-woven fabric is used for the surface layer covering sheet 5A, the liquid component of the soft feces can permeate from the permeable member 20 to the absorbent core 4 smoothly, and finally, can be retained in the absorbent core 4. Subsequently, the remained soft feces can also permeate through the permeable member 20 smoothly due to the retention of the liquid component of the soft feces in the absorbent core 4.

The basis weight of the surface layer covering sheet 5A is preferably 10 to 60 $g/m^2$. If the basis weight is smaller than 10 $g/m^2$ the mechanical strength is lowered. On the other hand, if the basis weight is larger than 60 $g/m^2$, the liquid component of the soft feces cannot be moved into the absorbent core 4 quickly, simultaneously, the sheet will be large meshed and the shutting ability of the super absorbent polymer is decreased. The surface layer covering sheet 5A can be defined by not only single layer but also laminated two or more layers, for example, three layers. When the surface layer covering sheet 5A is composed of the laminated plural layers, its basis weight is preferably 10 to 60 $g/m^2$.

On the other hand, as the other covering sheet 5C, a liquid permeable sheet such as crepe paper, a non-woven fabric, a perforated sheet can be used. Specifically, an absorbent sheet such as crepe paper is used preferably.

(Back Sheet)

The back sheet 2 formed at the under surface-side of the absorbent article is, in this embodiment, non-permeable sheet. Then, it is fabricated from, for example, a plastic sheet. The back sheet 2 may be pervious to air. The both side portions of the back sheet 2 are extended beyond the both side edges of the absorbent core AB. Then, a part of each extended side portion of the back sheet 2 is folded back to reach the wearer-side as a flap for covering the side portion of the face sheet 11.

(Permeating Speed of Soft Feces in Each Layer)

Here, it is determined that the permeating speed of soft feces in the face sheet 11 is designated by S1, the permeating speed of soft feces in the permeable member 20 is designated by S2 and the permeating speed of soft feces in the surface layer of the absorbent element (in this embodiment, the surface layer covering sheet 5A) is designated by S3. It is preferable that the relation among S1, S2 and S3 is S1>S2>S3.

It is necessary for the absorbent article that the soft feces are removed far away from the wearer's skin quickly and at the same time that the soft feces are contained and retained far away from the wearer's skin surely. In order to attain this, in the face sheet 11, the permeable member 20 and the surface layer covering sheet 5A, not only the high permeating speed of soft feces, but also the gradient of the permeating speed indicated by the above equation of inequality sign is necessary. Actually, the gradient of the permeating speed is more dominant than the absolute value of the permeating speed. Then, such gradient of the permeating speed of the soft feces improves the absorbing and retaining capacity for the urine and soft feces.

[Others]

The composition of the sanitary napkin in the embodiments stated before can be partly or totally applied to the absorbent pad in the embodiments stated above. Alternatively, the composition of the absorbent pad in the embodiments stated above can be partly or totally applied to the sanitary napkin in the embodiments stated before.

EXAMPLES

Experiment 1

Stiffness Test

As the binder, triacetin was used. By changing the basis weight of triacetin, several kinds of assemblies of fibers were provided. Then, several kinds of absorbent bodies (example 1 to 10 and comparative example 1 (in the absorbent body of the comparative example, the basis weight of binder is 0) formed by these assemblies were used as the samples.

Each sample was dried for 12 hours in a drafter adjusted at the temperature of 25° and the humidity of 60%. The thickness of the dried sample was used as the thickness before absorbing the body fluid. Next, 5 cc of horse blood was dropped freely to the dried sample and absorbed there. Then, this sample was left for 5 minutes. The thickness of such sample was used as the thickness after absorbing the body fluid. The thickness after absorbing the body fluid/the thickness before absorbing the body fluid was calculated. Thus, the result of such division was determined as the thickness sustainability. Large thickness sustainability means that the absorbent body can keep its stiffness, while the small thickness sustainability means that the absorbent body loses its stiffness. The thickness was measured with Handy-Type Compression Tester (KES-G5:KATO TECH CO., LTD.). The results of this test and the basis weight of the binder are shown in Table 1.

[Table 1]

Table 1 shows that, as for the assembly of fibers dispersed with the binder, its thickness sustainability was improved, which means that assembly did not lose its stiffness so easily. Additionally, when the basis weight of the dispersed binder was 17 g/m or more, the thickness sustainability was not significantly changed. Accordingly, when the triacetin is used as the binder, its preferable basis weight is about 16 to 18 g/m$^2$. The density of the assembly of fibers used as the sample was 30 g/m$^2$.

Experiment 2

Liquid Permeability Test

TABLE 1

| | Comparative example 1 | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Basis weight of triacetin (g/m$^2$) | 0 | 2.4 | 4.9 | 7.3 | 9.8 | 12.2 | 14.6 | 17.1 | 19.5 | 22.0 | 24.4 |
| Thickness before absorption (mm) | 22.0 | 21.0 | 20.0 | 18.0 | 18.0 | 17.0 | 17.0 | 16.5 | 16.5 | 16.0 | 14.5 |
| Thickness after absorption of 5 cc (mm) | 9.8 | 10.5 | 10.5 | 10.7 | 11.0 | 11.0 | 11.5 | 12.0 | 12.1 | 11.6 | 10.5 |
| Thickness sustainability (%) | 44.5 | 49.8 | 52.5 | 59.5 | 61.1 | 64.7 | 67.6 | 72.7 | 73.3 | 72.5 | 72.4 |

As the binder, triacetin was used. By changing the basis weight of triacetin, several kinds of assemblies A of fibers were provided. Then, these assemblies A were used in samples. In each sample, the top sheet C fabricated from a perforated film was laminated on the upper surface of the assemblies A of fibers while the absorbent member B fabricated from flocculent pulp was laminated on the under surface of the assemblies A of fibers. The top sheet, the assembly of fibers and the absorbent member were dried for 12 hours in a drafter adjusted at the temperature of 25° and the humidity of 60%. Additionally, a blank sample was provided for each test.

In each test, 5 cc of horse blood was dropped to the laminated sample from the top sheet-side and absorbed there and this was repeated 6 times at 20 minutes interval. Then, the absorption speed of the horse blood in each dropping was measured. The basis weights of the binders were same as in the stiffness test. The results are shown in Table 2.

[Table 2]

Table 2 shows that the absorption speed was improved by adding the binder so as to contact the fibers in the form of dot or line.

Therefore, by adding the binder so as to contact the fibers in the form of dot or line, the absorption speed as well as the thickness sustainability was improved. As a result, the absorbent body in accordance with the present invention excelled in body fluid permeability as well as in the fitting to the wearer.

Experiment 3

Pseudo feces were made in the image of soft feces. Then, the permeating speed of the pseudo feces was examined for a construction, which was adapted to be similar to that of an absorbent article as much as possible. The components of the pseudo feces are shown in the following.

| | |
|---|---|
| Component 1. starch (potato starch) | 3% |
| Component 2 starch (buckwheat flour) | 1.5% |
| Component 3 polishing powder (aluminum silicate) | 1.5% |
| Component 4 artificial urine | 94% |
| Surfactant | small amount |

For producing the pseudo feces having the above components, the following steps were carried out. (1) The component 1 was added into the component 4 and this was heated at 100° C. while it was stirred so that the potato starch was dissolved. (2) After its temperature was lowered to the room temperature, the component 2 was added. (3) Like step (2), the component 3 was added. (4) After the confirmation of homogeneous diffusion, the surfactant was added for adjusting the resultant mixture so as to have the surface tension of 28 dyne.

An absorbent pad was obtained by removing the permeable member 20 from the absorbent pad shown in FIGS. 43 and 44. Then, using this absorbent pad, an examination was performed for selecting the suitable material of the surface layer covering sheet 5A of the absorbent element AB. A spunbond non-woven fabric, which was fabricated PP, which had the basis weight of 35 g/m and which was perforated with through holes (diameter of 6.3 mm) arranged so as to have the space of 1.1 mm between adjacent holes in the longitudinal and width directions was used as the face sheet 11.

Each comparative sample was the flocculent pulp, which contained super absorbent polymer particles and which was covered with a crepe paper with its both side portions folded back around the side edges of the flocculent pulp. Then, the upper surface of the comparative sample 1 was not covered with the surface layer covering sheet 5A but exposed. On the

TABLE 2

| | Comparative example 1 | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Basis weight of binder (g/m$^2$) | 0.0 | 2.4 | 4.9 | 7.3 | 9.8 | 12.2 | 14.6 | 17.1 | 19.5 | 22.0 | 24.4 |
| Drop of 5 cc | 1.08 | 0.94 | 0.84 | 0.84 | 0.80 | 0.85 | 0.75 | 0.89 | 0.76 | 0.76 | 0.81 |
| Drop of 10 cc | 1.01 | 1.06 | 0.99 | 1.14 | 1.23 | 1.22 | 1.01 | 1.31 | 1.35 | 1.00 | 0.97 |
| Drop of 15 cc | 1.63 | 1.45 | 1.77 | 1.41 | 1.73 | 1.73 | 1.41 | 1.89 | 1.64 | 1.52 | 1.56 |
| Drop of 20 cc | 2.37 | 2.25 | 2.01 | 2.12 | 2.13 | 2.17 | 2.24 | 2.57 | 2.15 | 1.90 | 1.99 |
| Drop of 25 cc | 3.54 | 3.33 | 3.08 | 2.78 | 2.65 | 2.40 | 2.30 | 2.52 | 2.41 | 2.36 | 2.49 |
| Drop of 30 cc | 4.00 | 3.92 | 3.65 | 3.39 | 3.09 | 3.19 | 2.91 | 2.84 | 2.74 | 2.60 | 2.65 | other hand, the upper surface of the comparative sample 2 was covered with crepe paper as the surface layer covering sheet 5A while the upper surface of the comparative samples 3 to 5 were covered with an airthrough non-woven fabric as the surface layer covering sheets 5A.

For each comparative sample, the cylinder (diameter of 3 inc.) was disposed on the face sheet 11 and 50 cc of the above pseudo feces (colored) was continuously poured into the cylinder with the rate of 15 cc/sec. The absorption speed was defined as the time (sec) taken from when the pouring was started to when the pseudo feces cannot be seen visually. Further, after the absorption, the degree of strike through was determined qualitatively. The results are shown in Table 3.

[Table 3]

From the experiment 3, the following facts are known. As for the permeating, absorbing, and retaining, the sample, which is not provided with the surface layer covering sheet 5A, and the sample, which is covered with the crepe paper as the surface layer covering sheet 5A, had poor capacity, while the samples, which were covered with the airthrough non-woven fabrics as the surface layer covering sheets 5A, had high capacity.

Experiment 4

It is found that the airthrough non-woven fabric was preferably used as the surface layer covering sheet 5A from the experiment 3. Thus, in experiment 4, all of the absorbent elements AB were provided with the airthrough non-woven fabrics as the surface layer covering sheets 5A. On such condition, the experiment 4 was performed for selecting the preferable material of the permeable member 20. This experiment was progressed in the same manner as the experiment 3 except that the components of the pseudo feces were different a little from those of experiment 3 as shown in the following.

| Component 1. starch (potato starch) | 6% |
| Component 2 starch (buckwheat flour) | 3% |
| Component 3 polishing powder (aluminum silicate) | 3% |
| Component 4 artificial urine | 88% |
| Surfactant | small amount |

The results are shown in Table 4.

[Table 4]

From Table 4, it is found that the absorption speed was small in both of the permeable sheet fabricated from the assembly of hydrophilic filaments in opened tows and the permeable member fabricated from the water repellent airthrough non-woven fabric. On the contrary, it is found that the absorption speed was very high in the permeable sheet fabricated from the assembly of water repellent filaments in opened tows.

Experiment 5

In the experiment 5, perforated sheets each having the diameter of through hole of 3 mm$^2$ or smaller (including non-perforated sheet) were used as the face sheets 11. Then, it is found that such face sheets 11 have low permeability of the pseudo feces, whatever changed their open area rates and materials may be.

Experiment 6

In the experiment 6, the assembly of water repellant and spirally crimped filaments in opened tows was used as the permeable member. Then, it is found that such permeable member 20 has higher absorption speed comparing the case that the filaments are not crimped.

TABLE 3

|  | Comparative sample 1 | Comparative sample 2 | Comparative sample 3 | Comparative sample 4 | Comparative sample 5 |
| --- | --- | --- | --- | --- | --- |
| Face sheet | Blank | Crepe paper | Airthrough | Airthrough | Airthrough |
| Basis weight |  | 15 g/m$^2$ | 21 g/m$^2$ | 30 g/m$^2$ | 40 g/m$^2$ |
| Components etc |  | Proportion of Crepe 15% | PE/PP 2.2d | PE/PP 5.6d | PE/PP 6.0d |
| Absorbing speed (sec) | 155 | 600< | 563 | 362 | 283 |
| Evaluation for strike through | x | x | Δ | ○ | ○ |

TABLE 4

| Permeable sheet | Comparative example 2 | Comparative example 3 | Comparative example 4 | Example 11 |
| --- | --- | --- | --- | --- |
| Producing method | Sheet of opened tow (Assembly of filaments) | Sheet of opened tow (Assembly of filaments) | Airthrough non-woven fabric | Sheet of opened tow (Assembly of filaments) |
| Kind of fiber | Acetate | Acetate | PET/PE | PET/PE |
| Hydrophilic or water repellent | Hydrophilic | Hydrophilic | Water repellent | Water repellent |
| Fineness of fiber | 4d | 4d | 3d | 3d |
| Basis weight | 50 g/m$^2$ | 100 g/m$^2$ | 50 g/m$^2$ | 50 g/m$^2$ |
| Absorbing speed (sec) | 600< | 600< | 600< | 20 |
| Evaluation for strike through | x | x | x | ○ |

INDUSTRIAL APPLICABILITY

The body fluid absorbent article in accordance with the present invention can be applied to a general article absorbing the body fluid such as urine, menstrual blood, or the like. As the body fluid absorbent article of this kind, there can be exemplified a disposable diaper, a sanitary napkin, a urine pad, an incontinence pad or the like. This invention is most preferably applied to sanitary napkins.

BRIEF DESCRIPTION OF THE DRAWINGS

FIG. 49 is a plan view of a developed absorbent article for explaining the arrangement of filaments.

EXPLANATION OF REFERENCE

Figure 1:
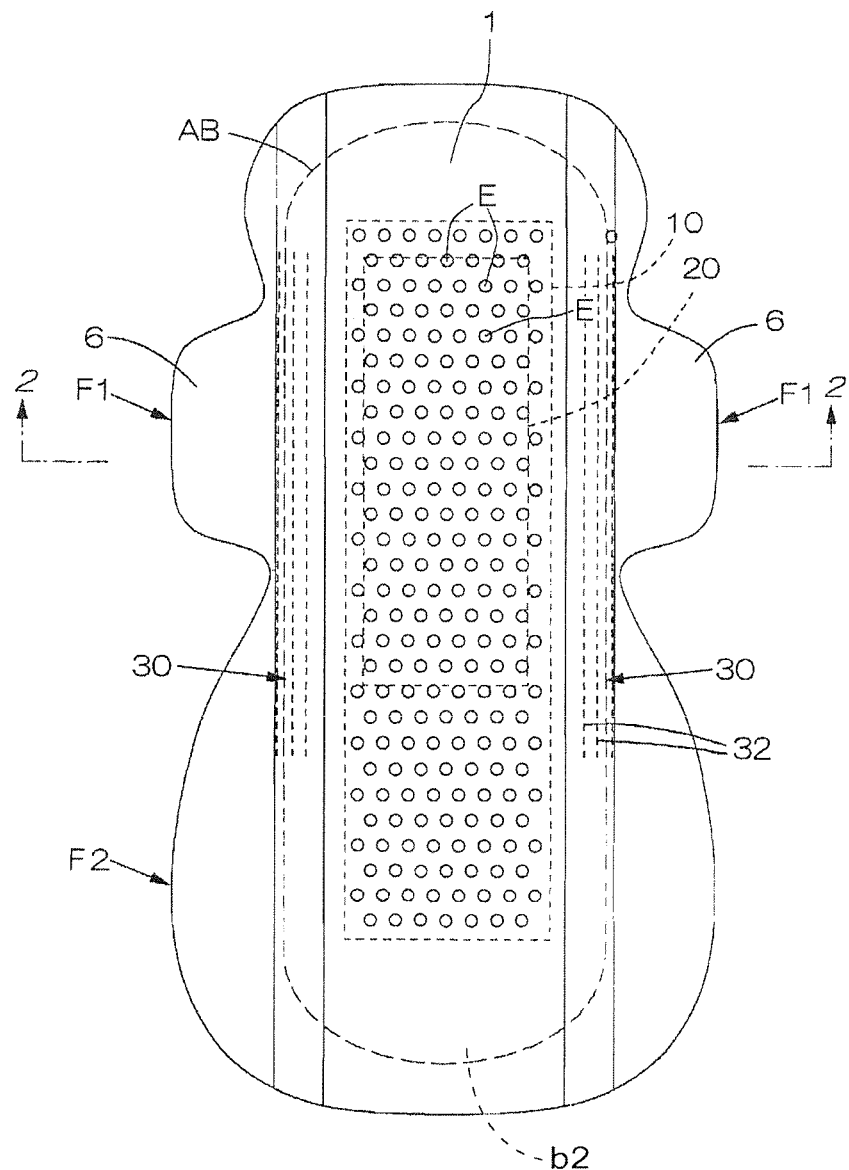
FIG. 1 is a plan view of an absorbent article.
Figure 2:
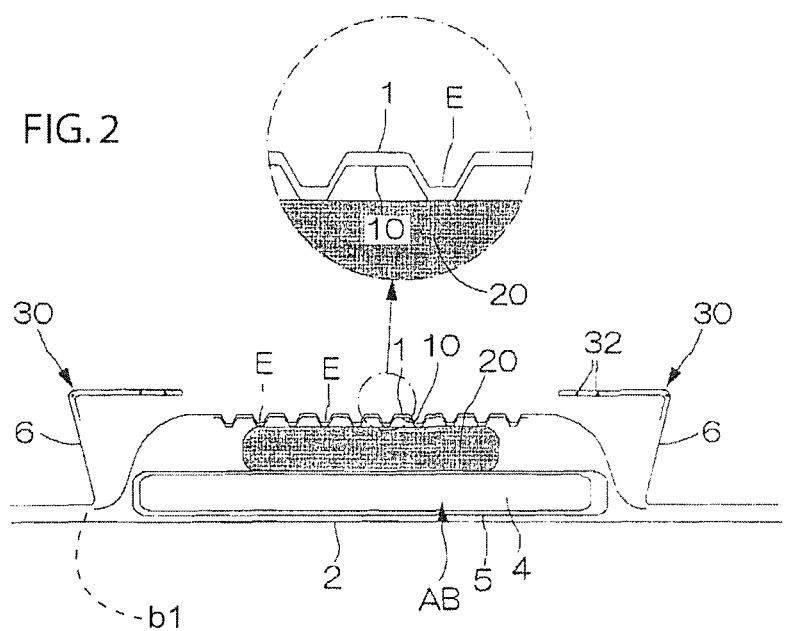
FIG. 2 is a schematic cross section of an absorbent article.
Figure 3:
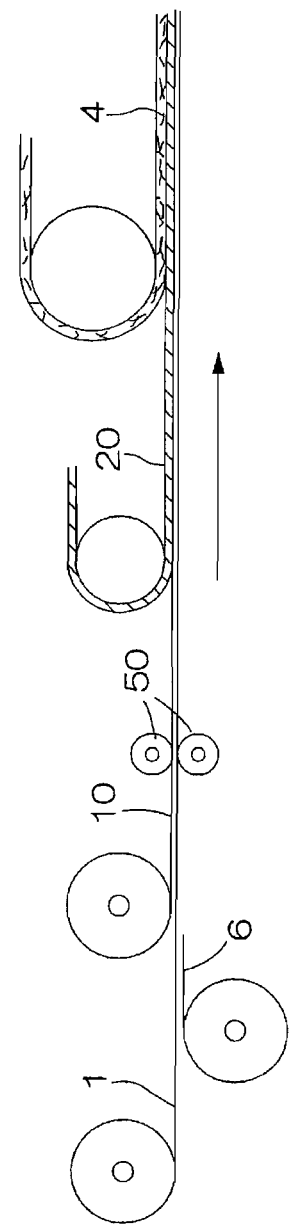
FIG. 3 is a schematic illustration showing a producing method and apparatus.
Figure 4:
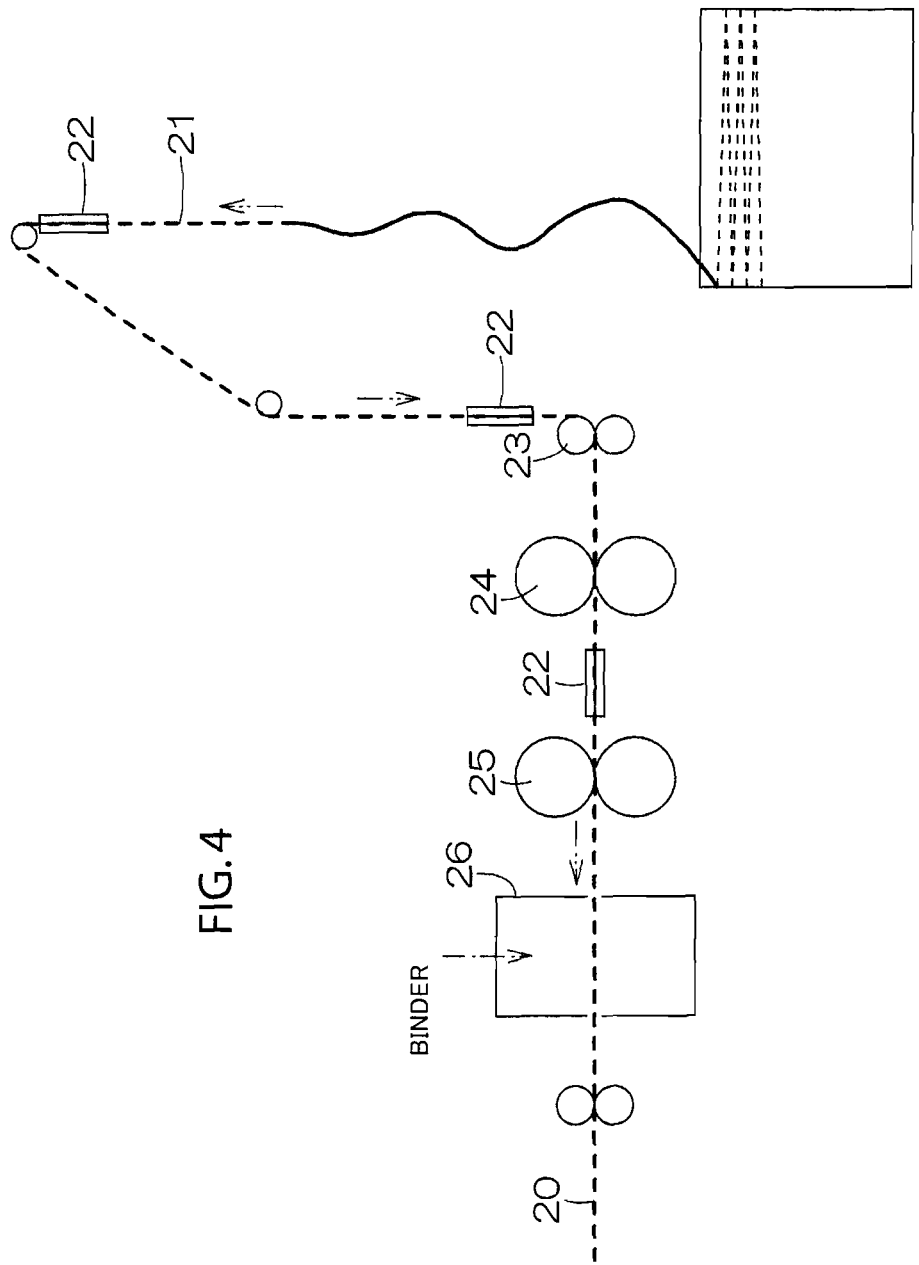
FIG. 4 is a schematic illustration showing a producing flow of an assembly of fibers.
Figure 5:
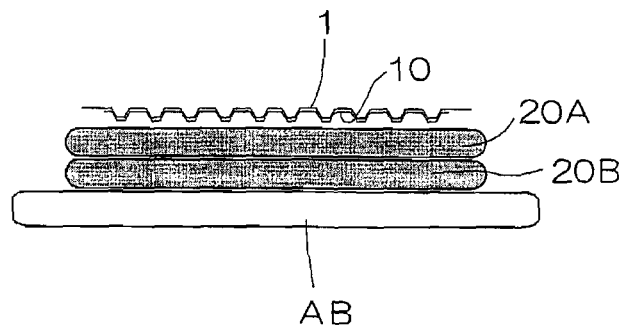
FIG. 5 is a cross section showing schematically the first embodiment related to the laminating of an assembly of fibers.
Figure 6:
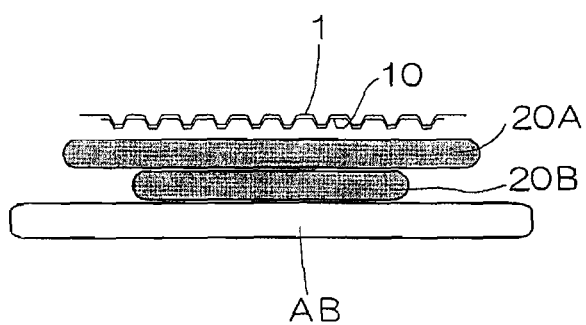
FIG. 6 is a cross section showing schematically the second embodiment related to the laminating of an assembly of fibers.
Figure 7:
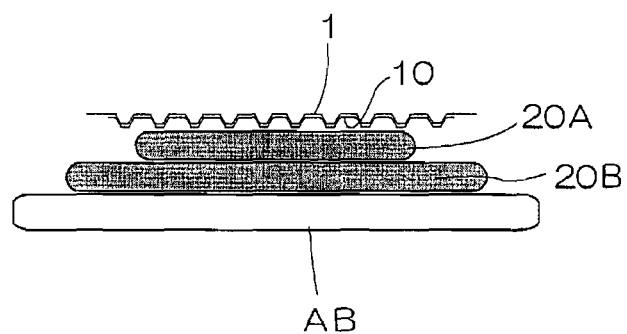
FIG. 7 is a cross section showing schematically the third embodiment related to the laminating of an assembly of fibers.
Figure 8:
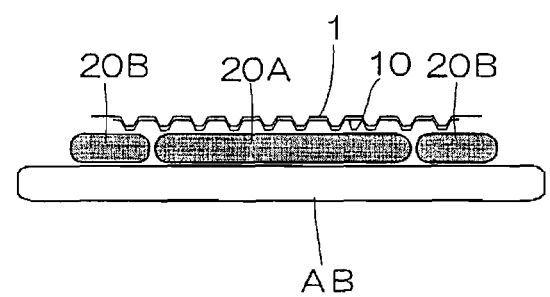
FIG. 8 is a cross section showing schematically the fourth embodiment related to the laminating of an assembly of fibers.
Figure 9:
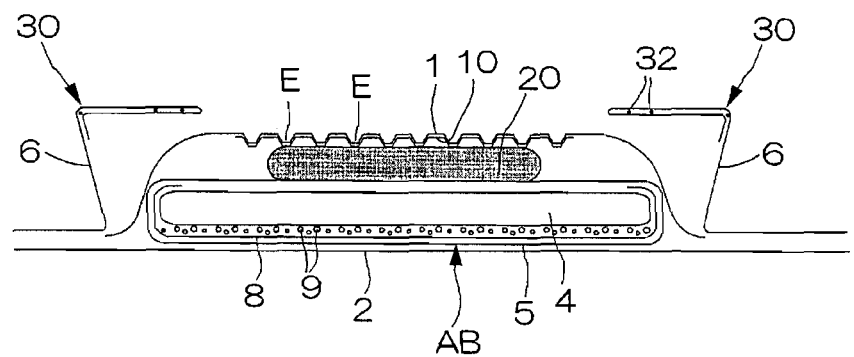
FIG. 9 is a schematic cross section of an absorbent article.
Figure 10:
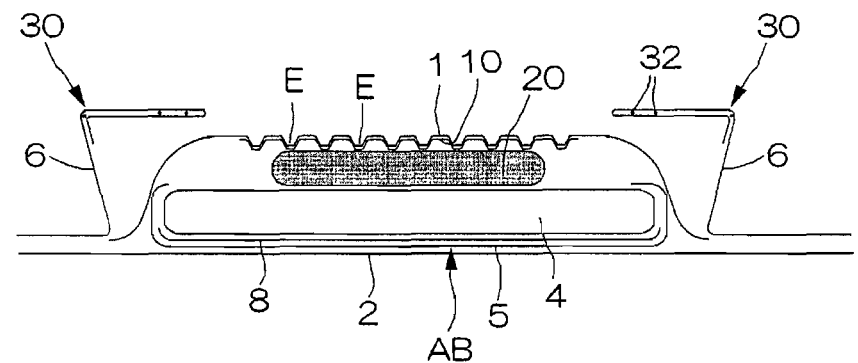
FIG. 10 is a schematic cross section of an absorbent article.
Figure 11:
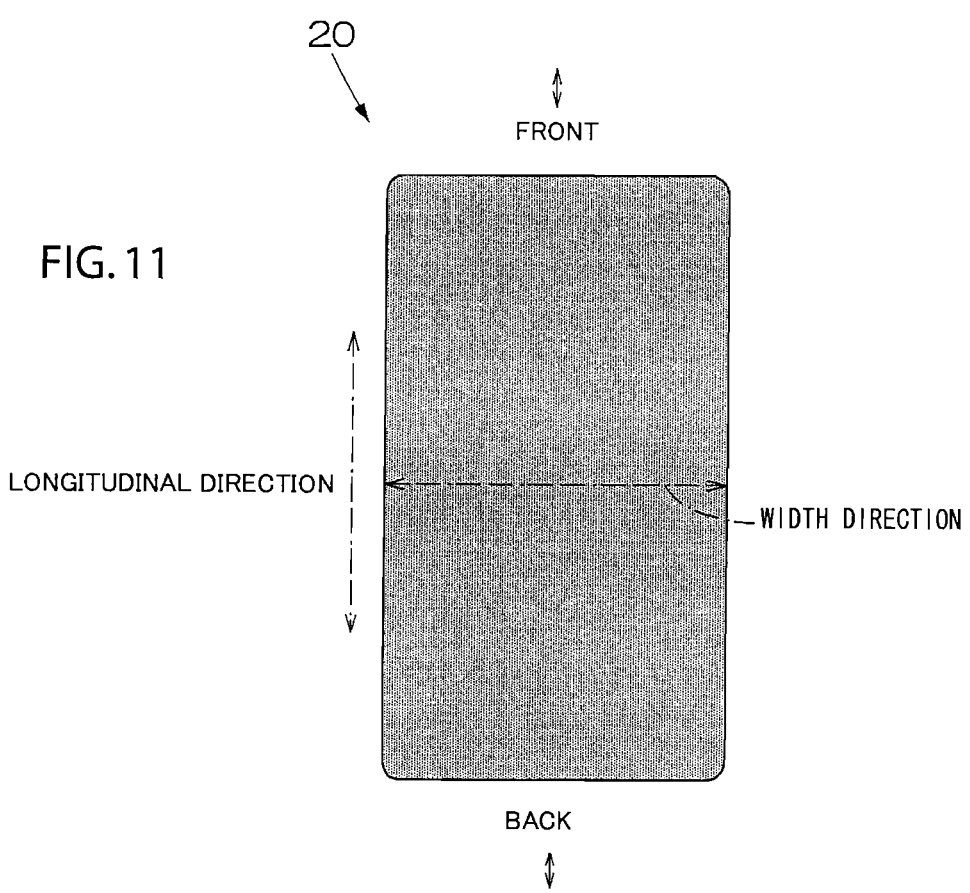
FIG. 11 is a plan view showing schematically the first embodiment of an assembly of fibers.
Figure 12:
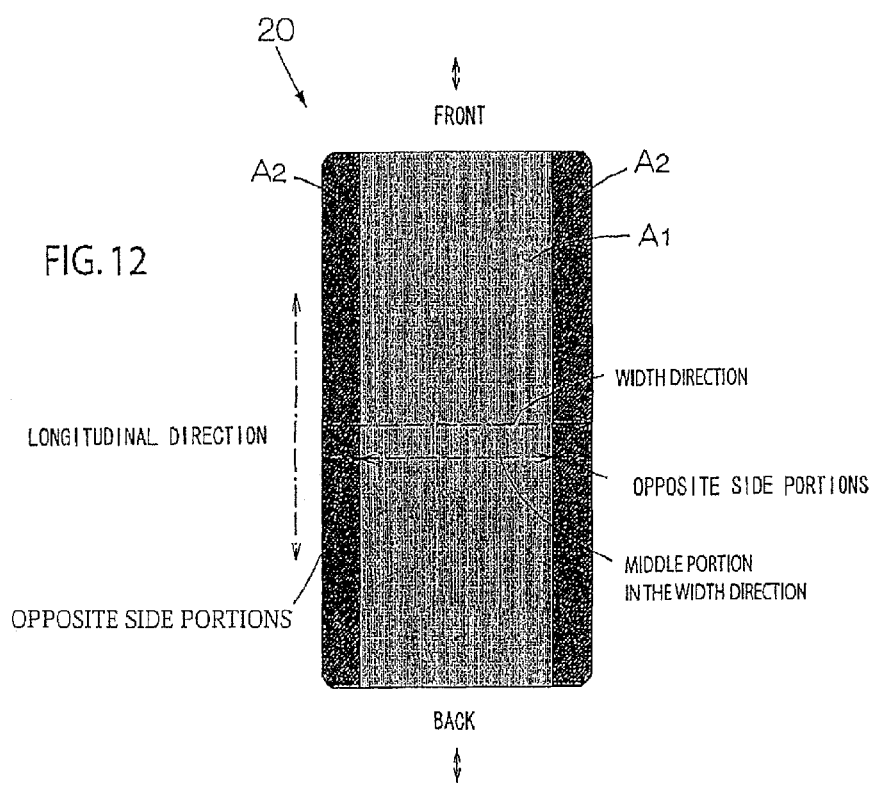
FIG. 12 is a plan view showing schematically the second embodiment of an assembly of fibers.
Figure 13:
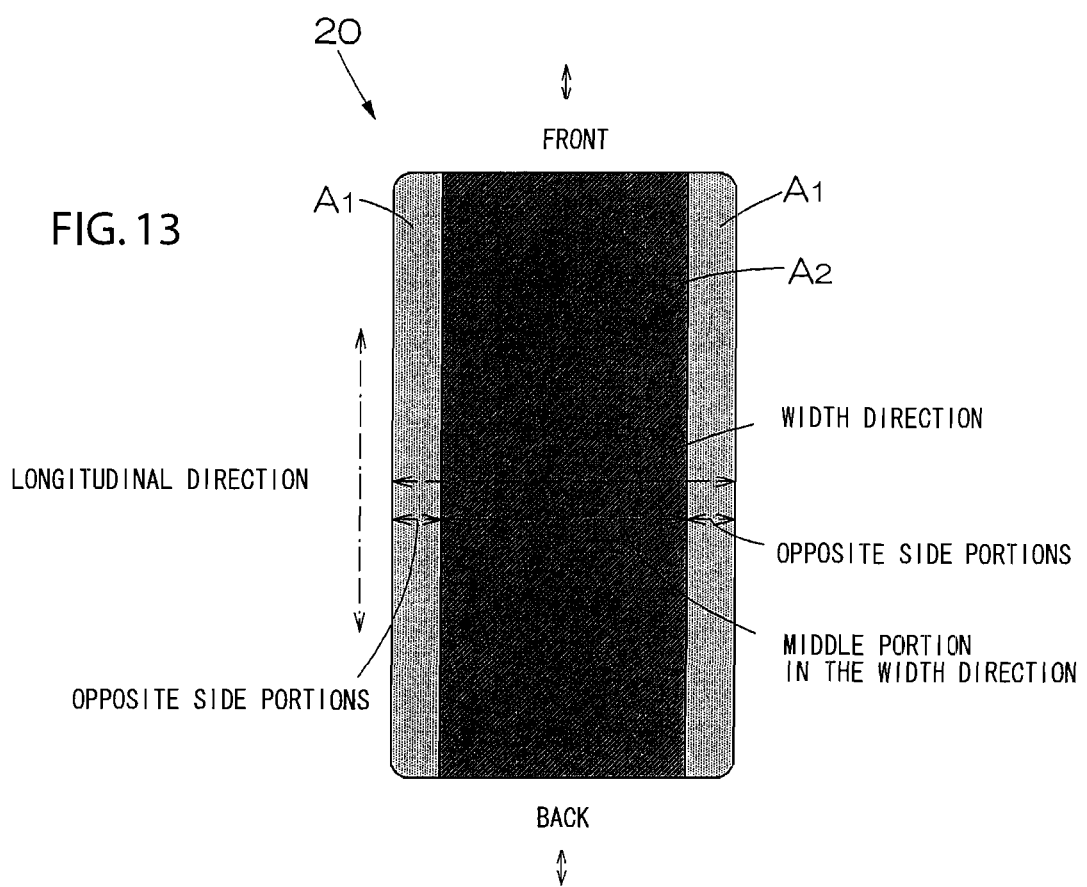
FIG. 13 is a plan view showing schematically the third embodiment of an assembly of fibers.
Figure 14:
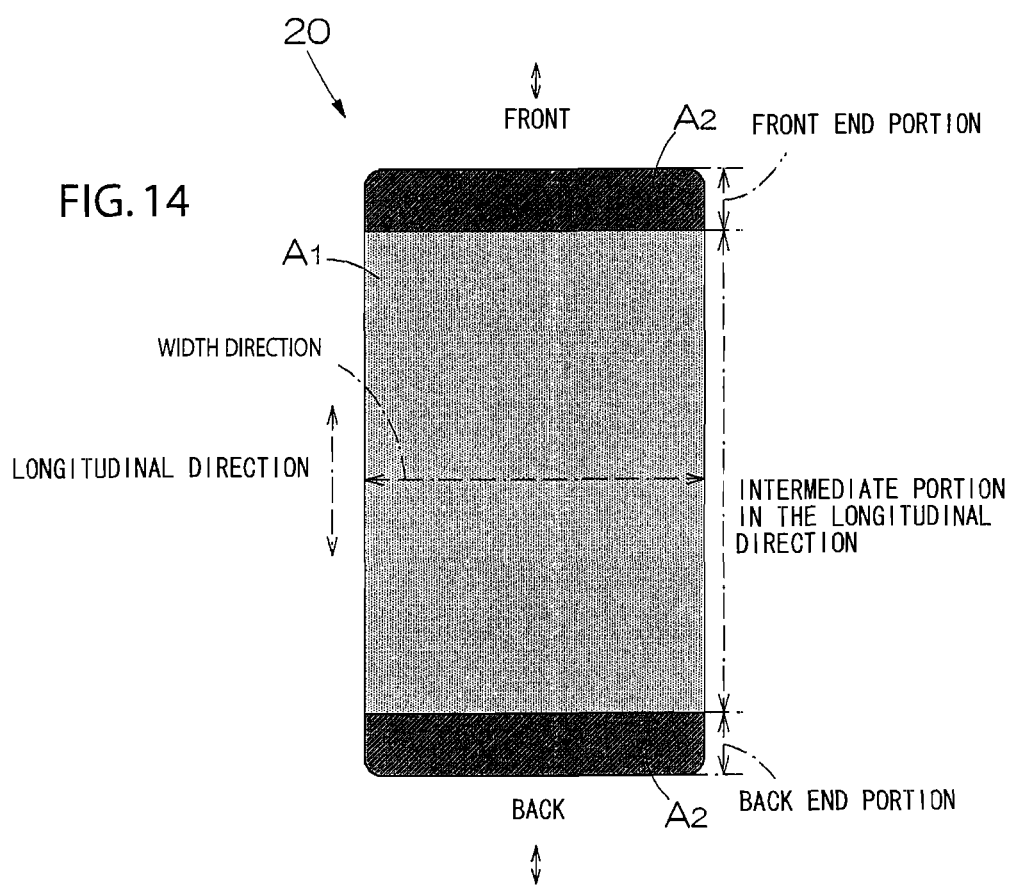
FIG. 14 is a plan view showing schematically the fourth embodiment of an assembly of fibers.
Figure 15:
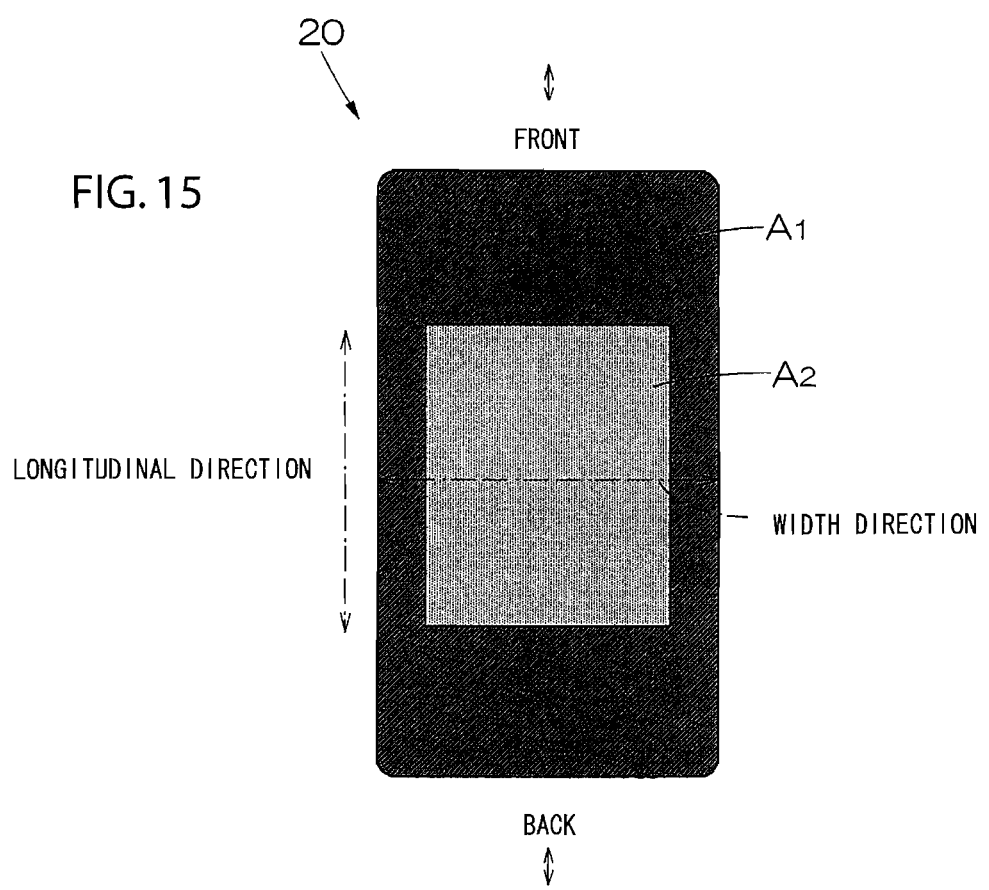
FIG. 15 is a plan view showing schematically the fifth embodiment of an assembly of fibers.
Figure 16:
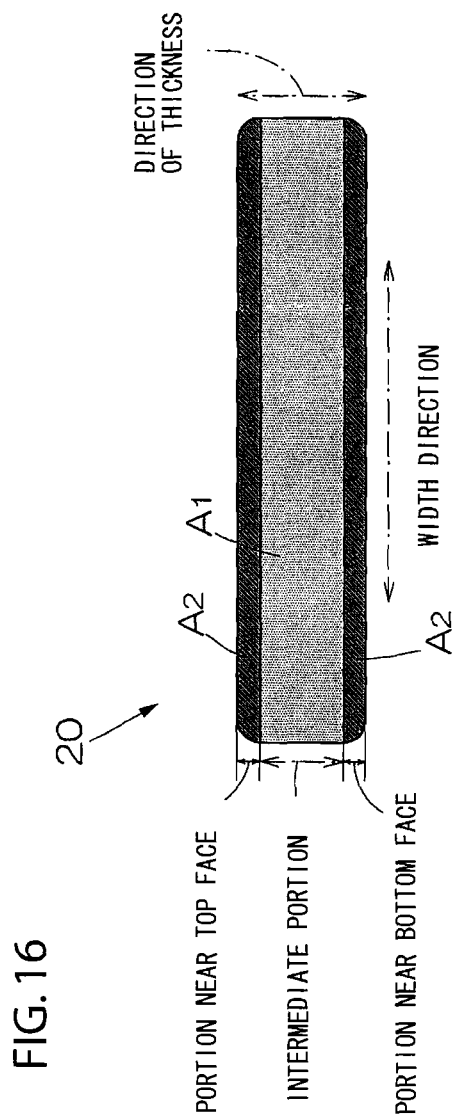
FIG. 16 is a cross section showing schematically the sixth embodiment of an assembly of fibers.
Figure 17:
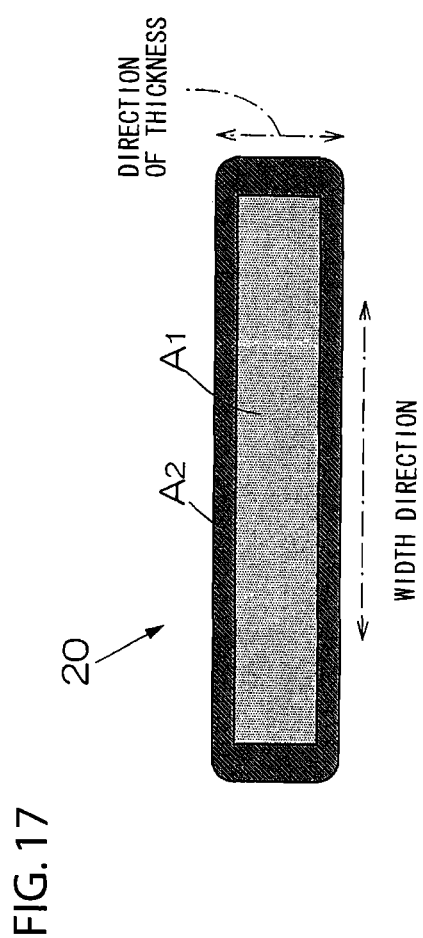
FIG. 17 is a cross section showing schematically the seventh embodiment of an assembly of fibers.
Figure 18:
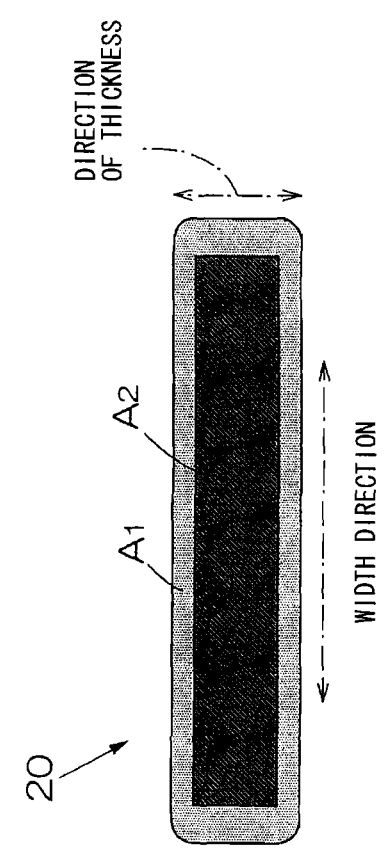
FIG. 18 is a cross section showing schematically the eighth embodiment of an assembly of fibers.
Figure 19:
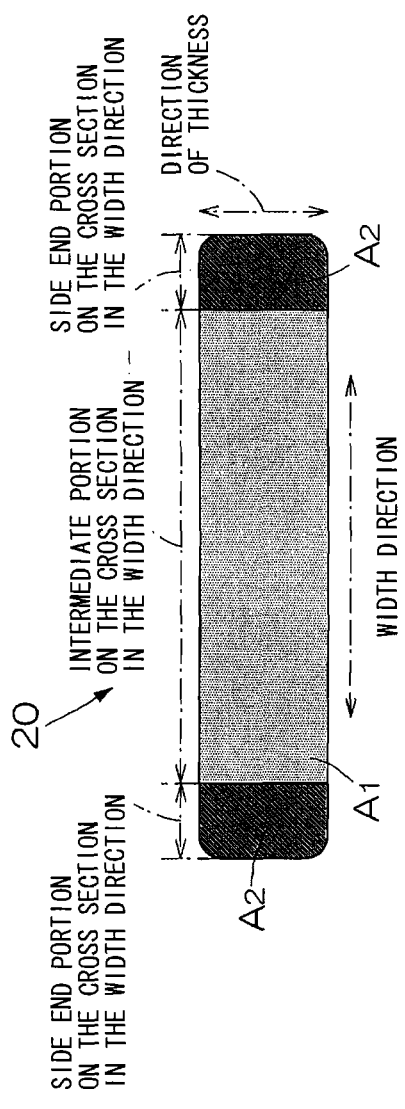
FIG. 19 is a cross section showing schematically the ninth embodiment of an assembly of fibers.
Figure 20:
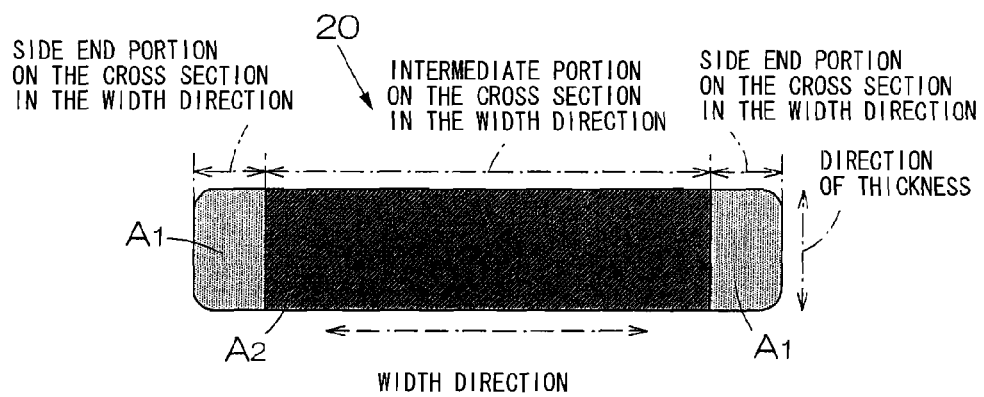
FIG. 20 is a cross section showing schematically the tenth embodiment of an assembly of fibers.
Figure 21:
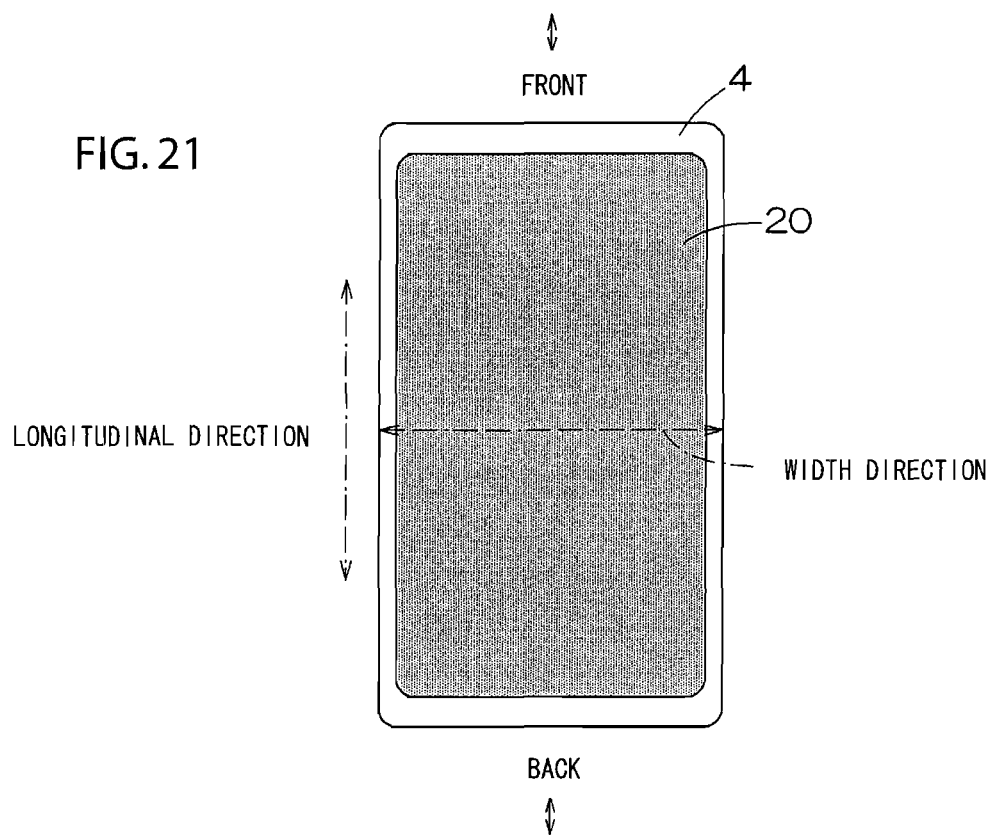
FIG. 21 is a plan view showing schematically the first embodiment of laminating.
Figure 22:
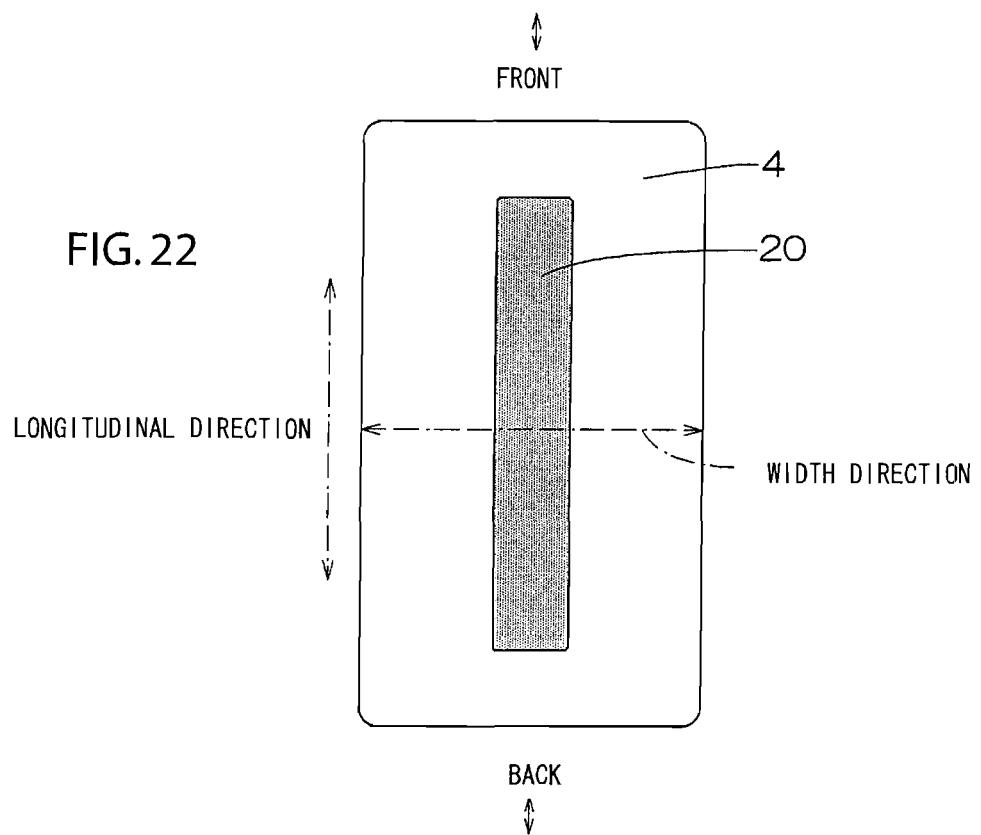
FIG. 22 is a plan view showing schematically the second embodiment of laminating.
Figure 23:
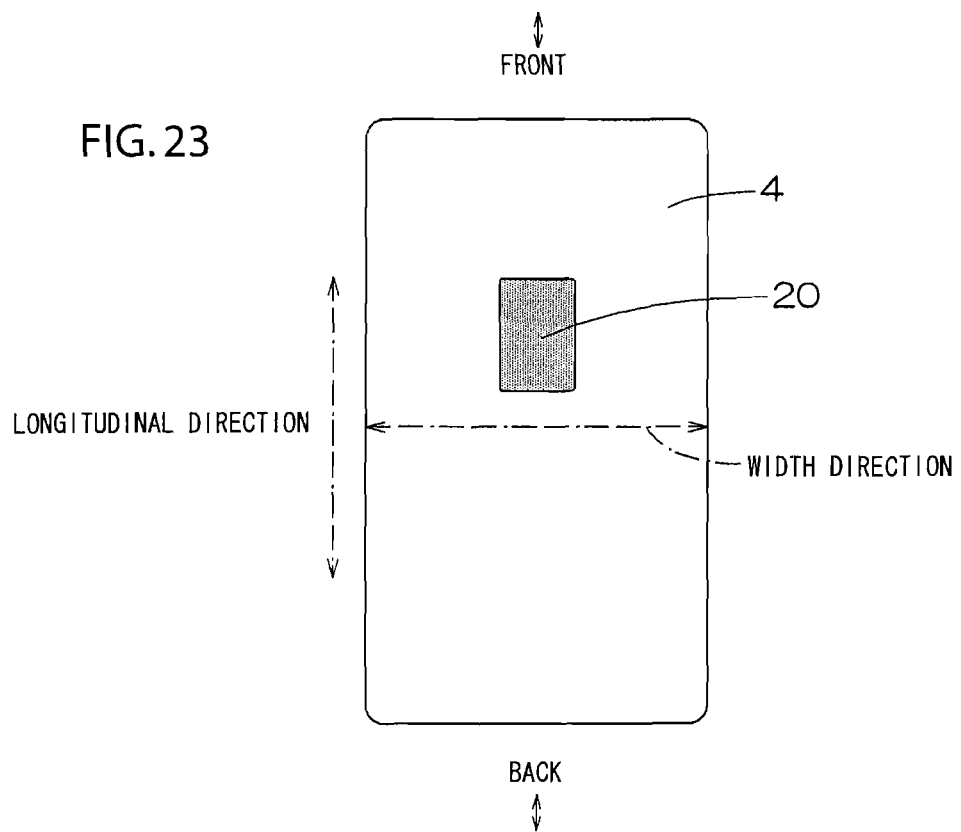
FIG. 23 is a plan view showing schematically the third embodiment of laminating.
Figure 24:
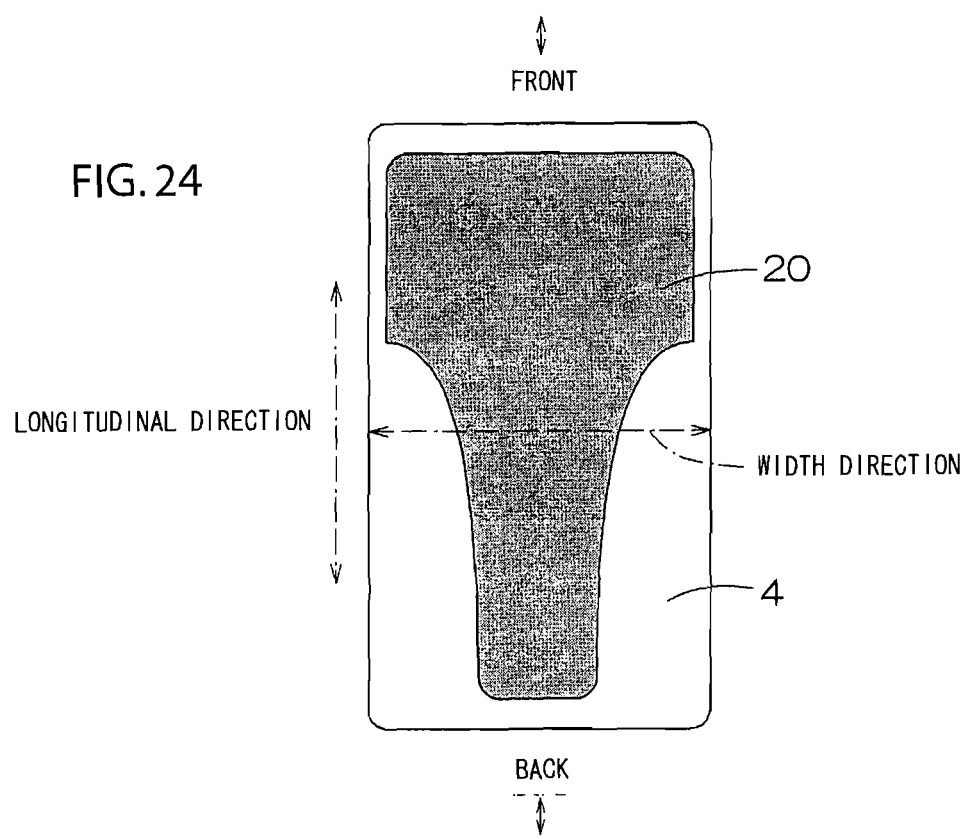
FIG. 24 is a plan view showing schematically the fourth embodiment of laminating.
Figure 25:
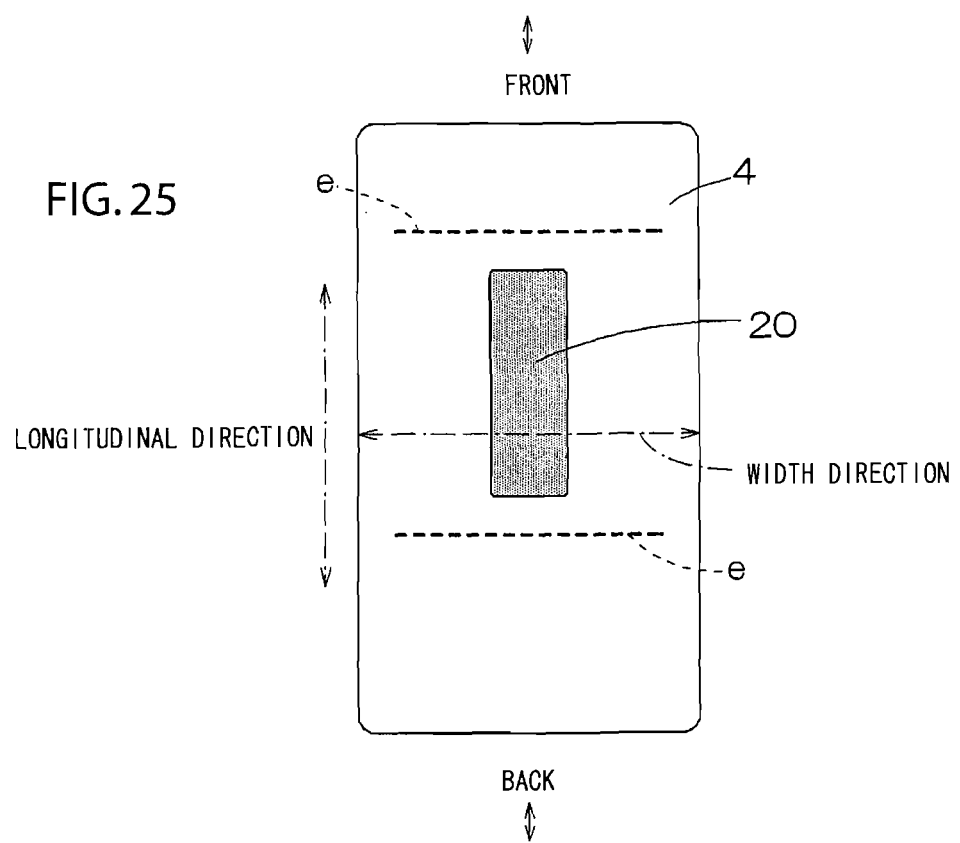
FIG. 25 is a plan view showing schematically the first embodiment of embossing.
Figure 26:
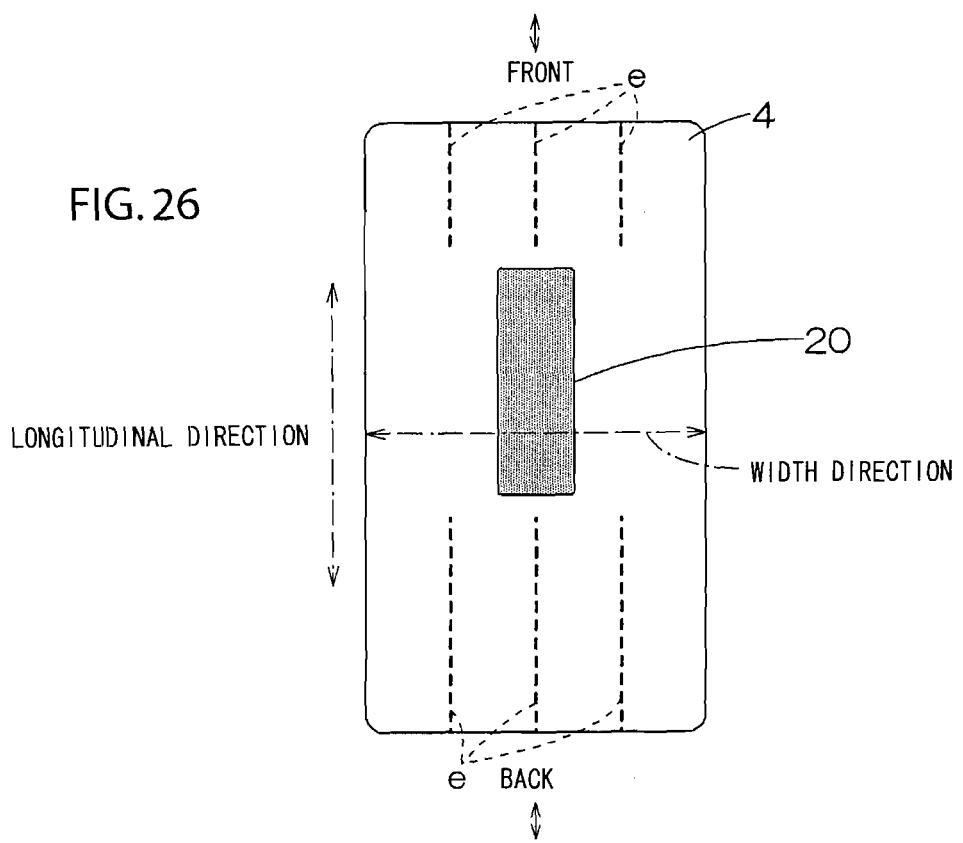
FIG. 26 is a plan view showing schematically the second embodiment of embossing.
Figure 27:
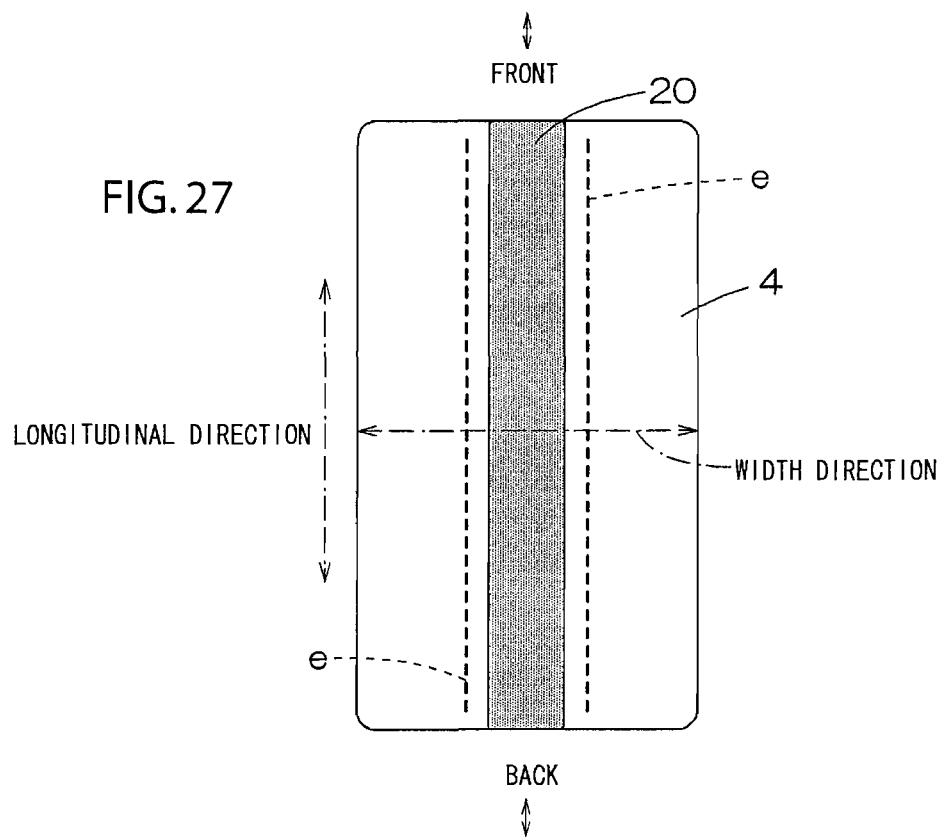
FIG. 27 is a plan view showing schematically the third embodiment of embossing.
Figure 28:
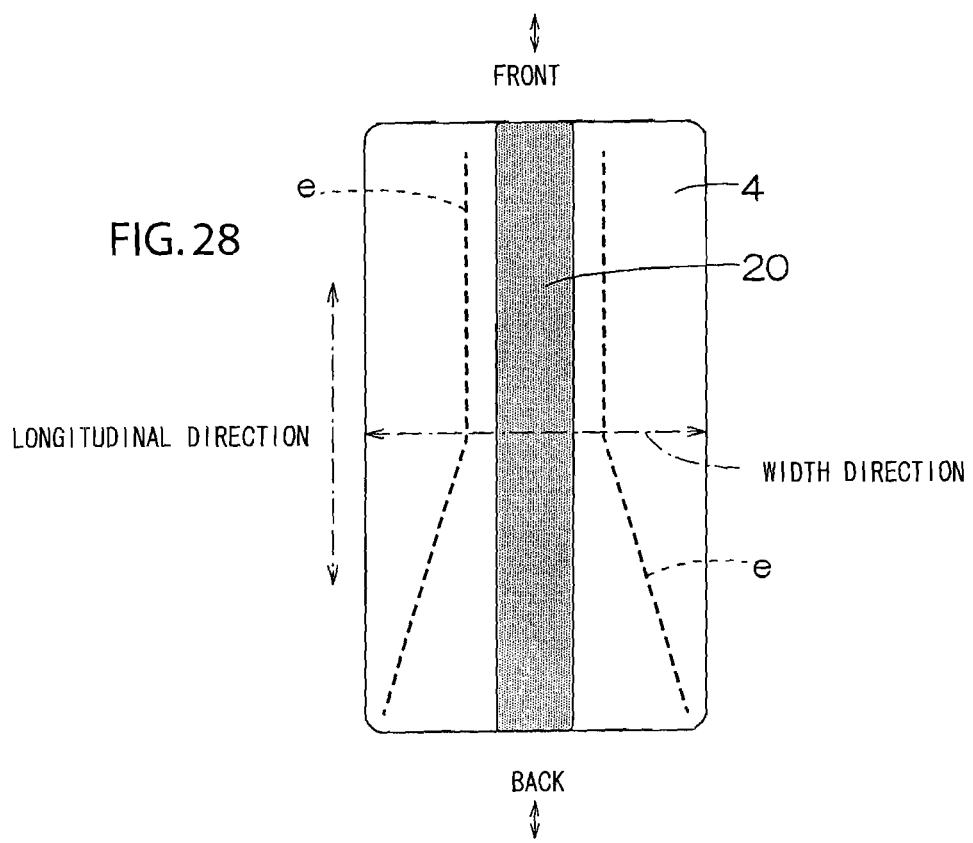
FIG. 28 is a plan view showing schematically the fourth embodiment of embossing.
Figure 29:
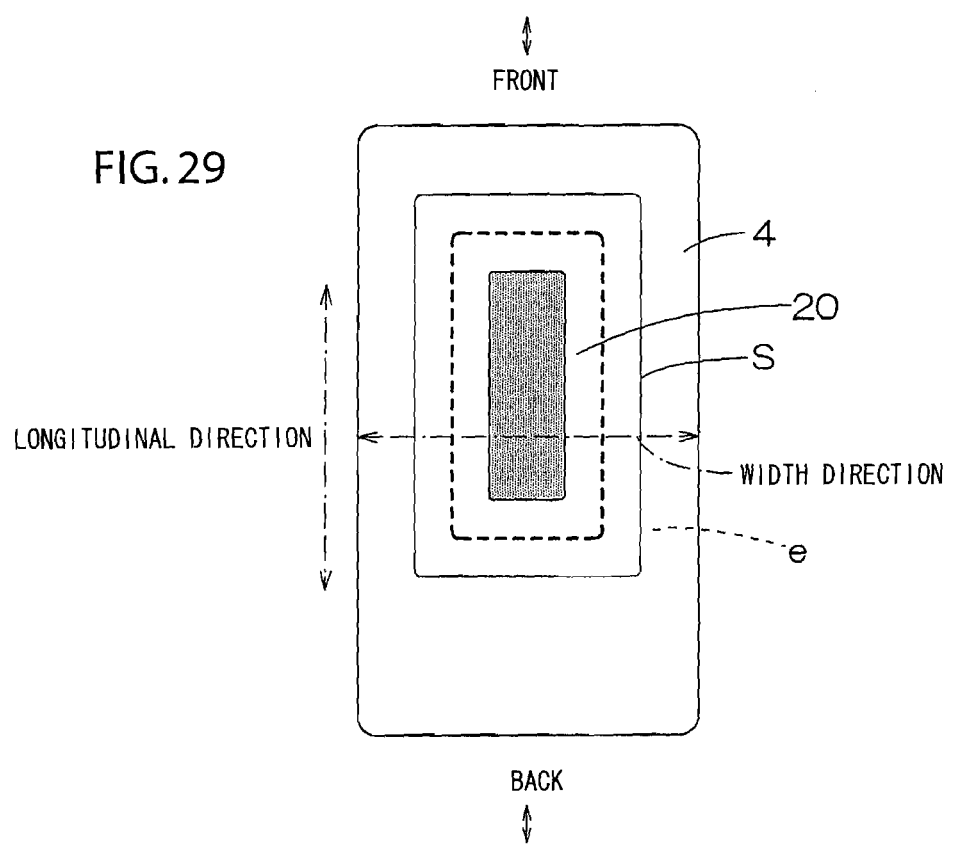
FIG. 29 is a plan view showing schematically the fifth embodiment of embossing.
Figure 30:
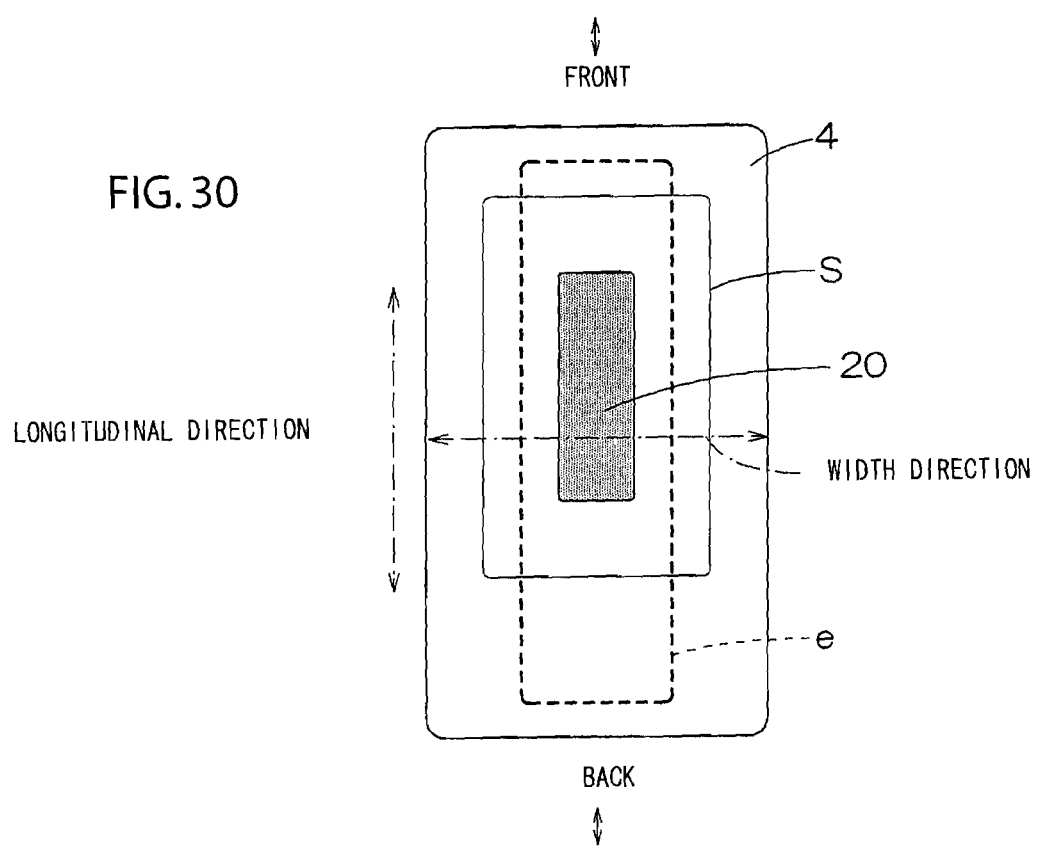
FIG. 30 is a plan view showing schematically the sixth embodiment of embossing.
Figure 31:
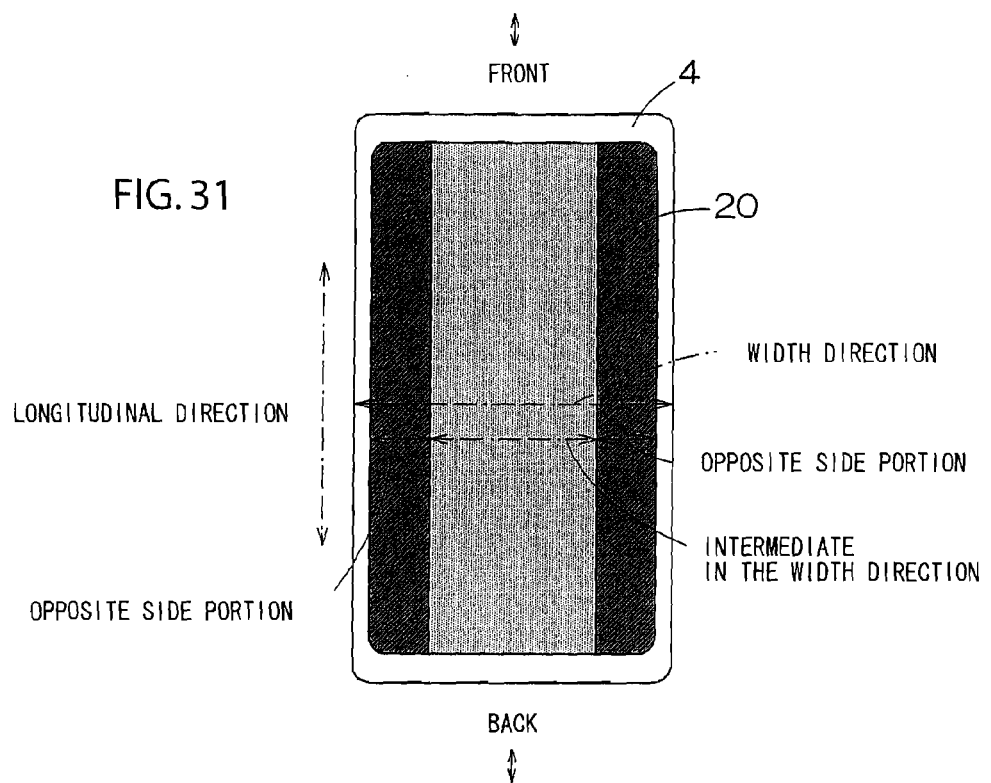
FIG. 31 is a plan view showing schematically the fifth embodiment of laminating.
Figure 32:
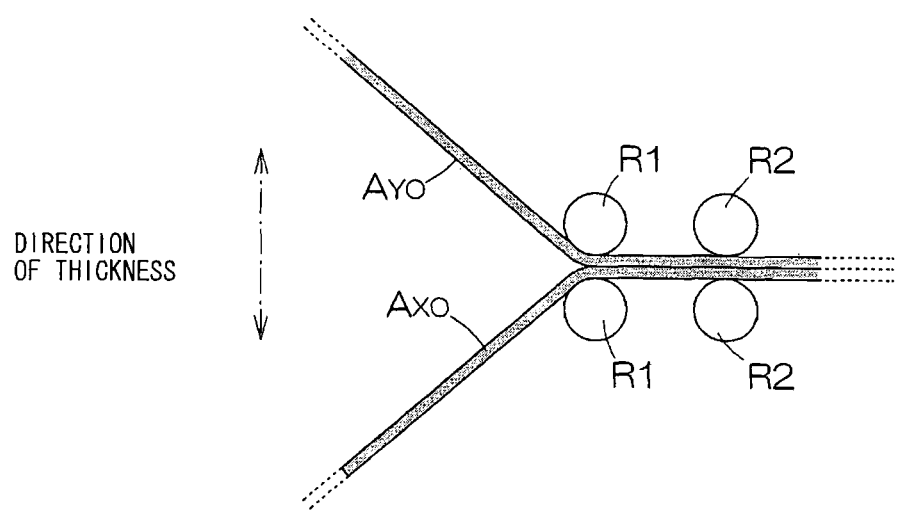
FIG. 32 is a schematic illustration showing the producing method of an assembly of fibers having laminating configuration.
Figure 33:
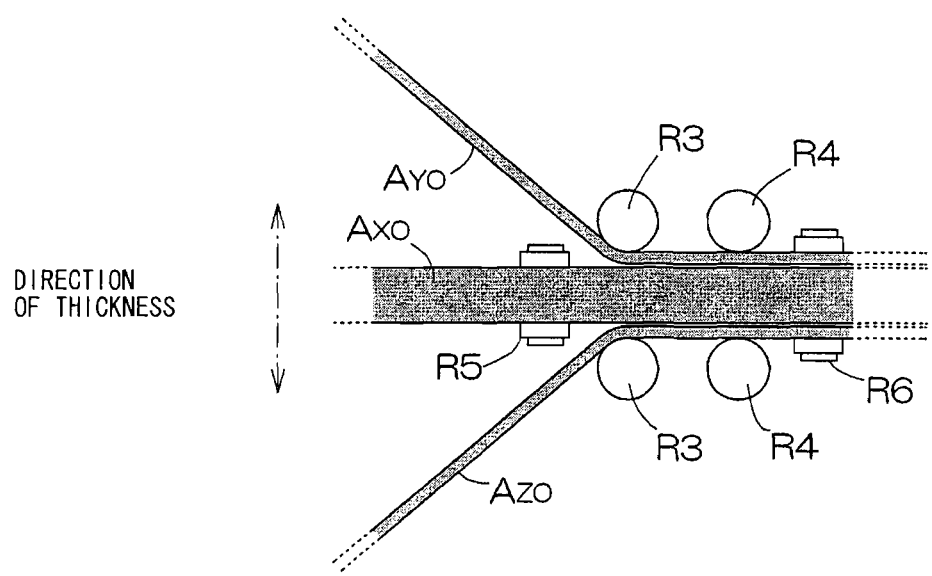
FIG. 33 is a schematic illustration showing the producing method of assemblies of fibers arranged separately side by side in the width direction.
Figure 34:
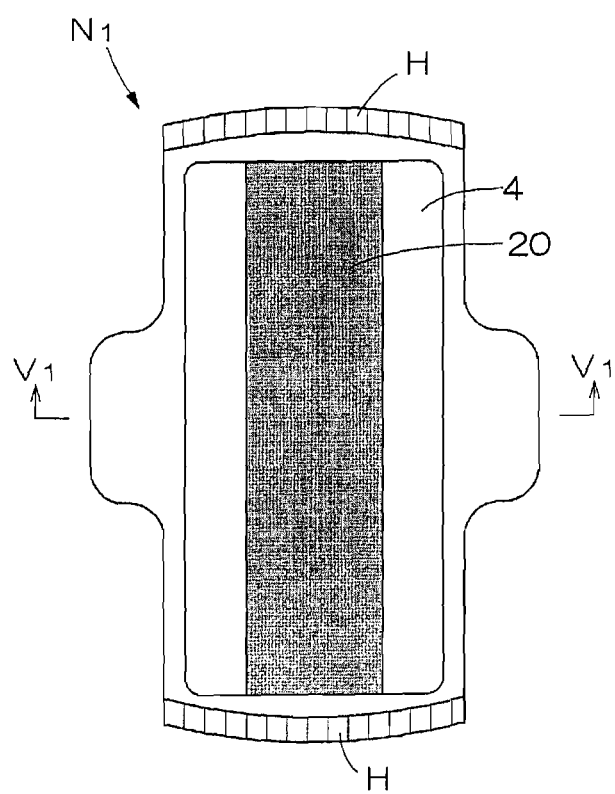
FIG. 34 is a plan view showing schematically the first embodiment of a sanitary napkin.
Figure 35:
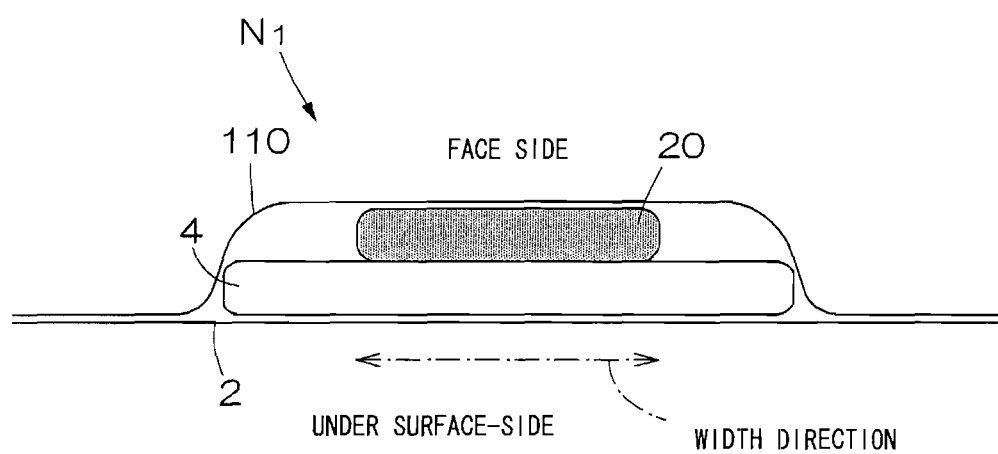
FIG. 35 is a cross section showing schematically the first embodiment of a sanitary napkin.
Figure 36:
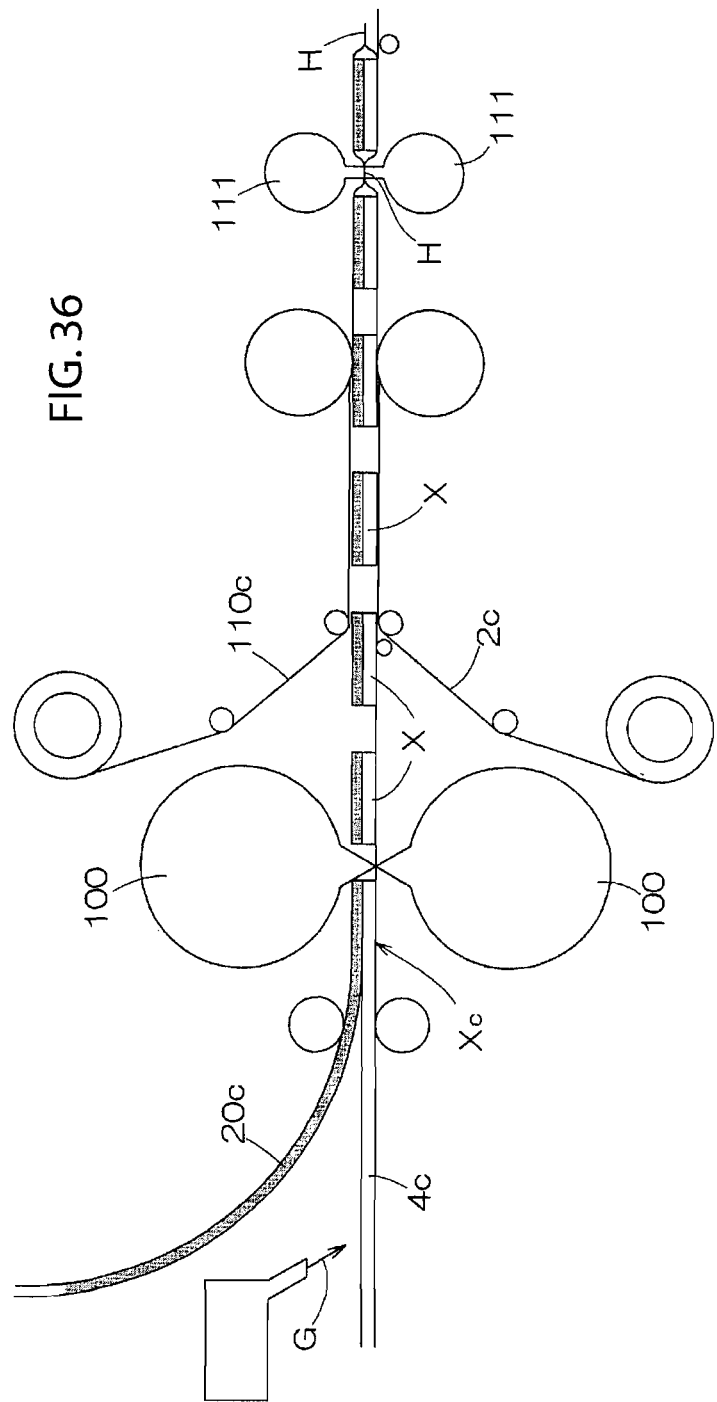
FIG. 36 is a schematic illustration for explaining the producing method of the first embodiment of a sanitary napkin.
Figure 37:
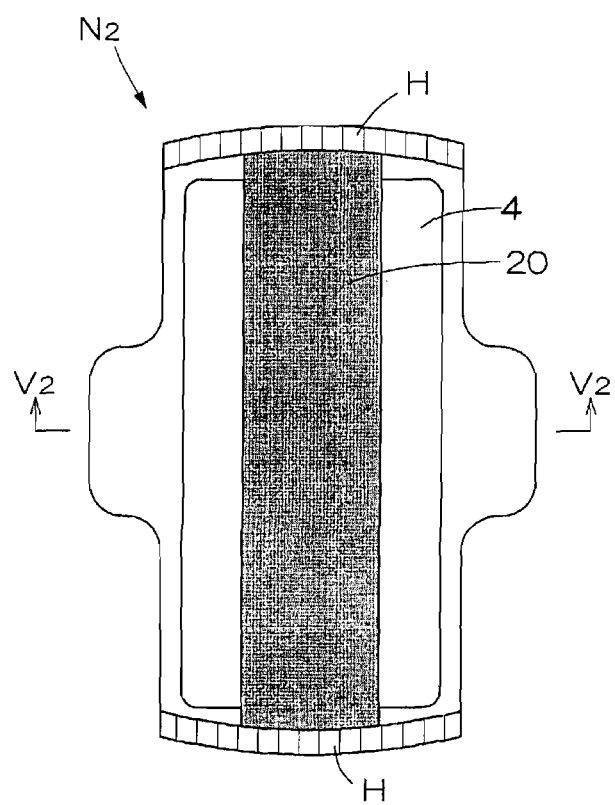
FIG. 37 is a plan view showing schematically the second embodiment of a sanitary napkin.
Figure 38:
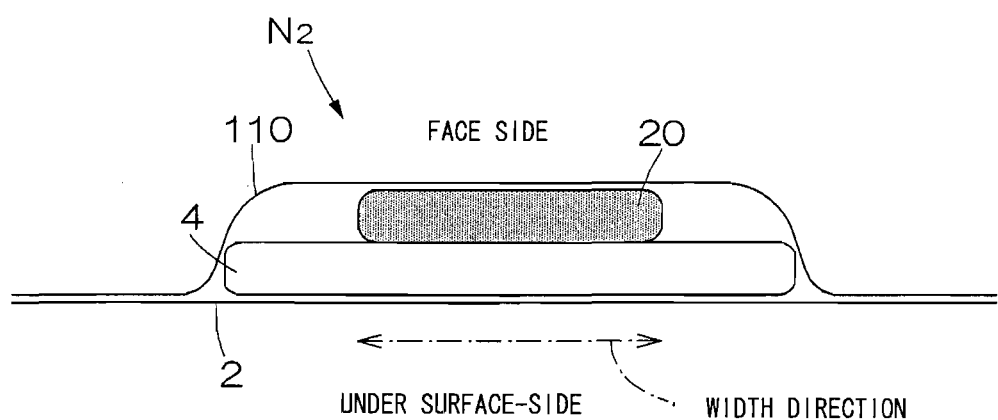
FIG. 38 is a cross section showing schematically the second embodiment of a sanitary napkin.
Figure 39:
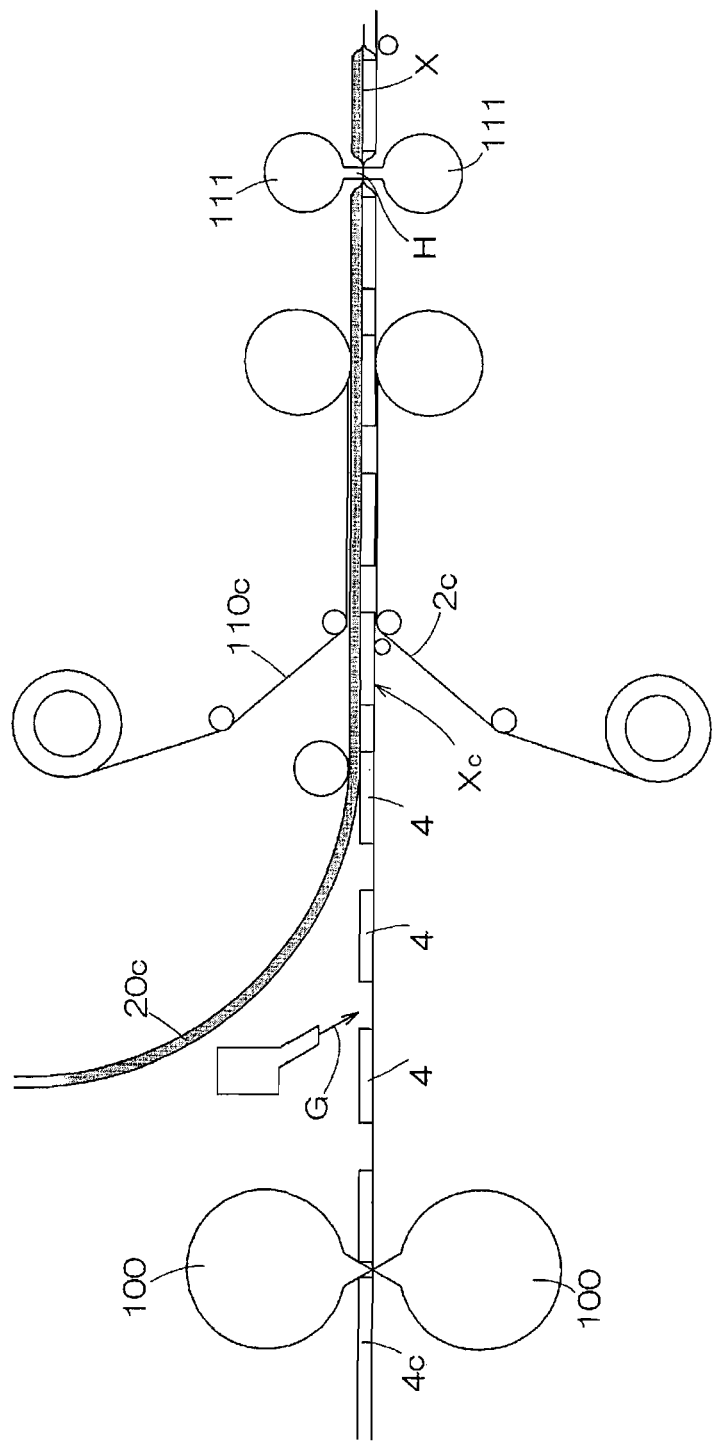
FIG. 39 is a schematic illustration for explaining the producing method of the second embodiment of a sanitary napkin
Figure 40:
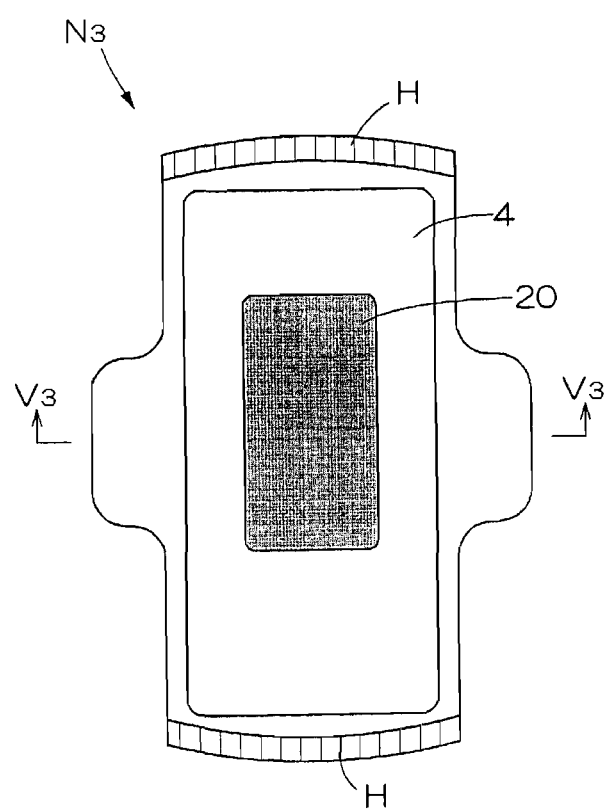
FIG. 40 is a plan view showing schematically the third embodiment of a sanitary napkin.
Figure 41:
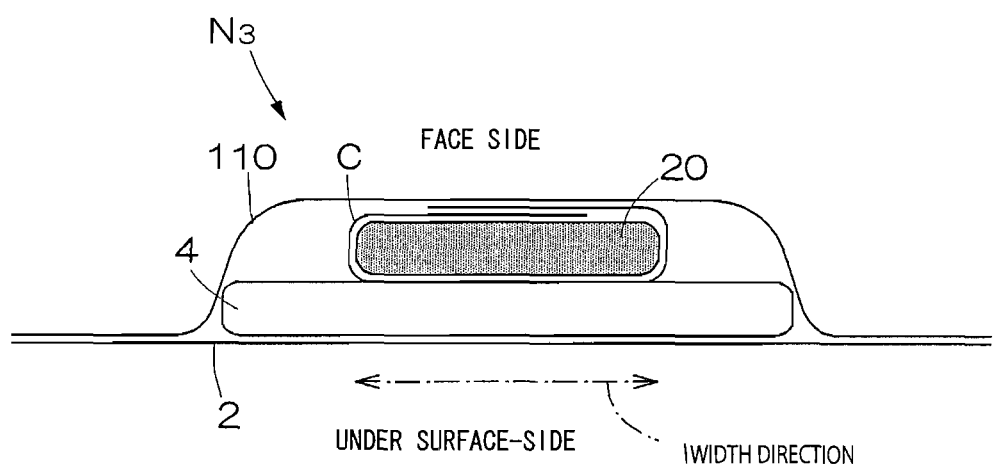
FIG. 41 is a cross section showing schematically the third embodiment of a sanitary napkin.
Figure 42:
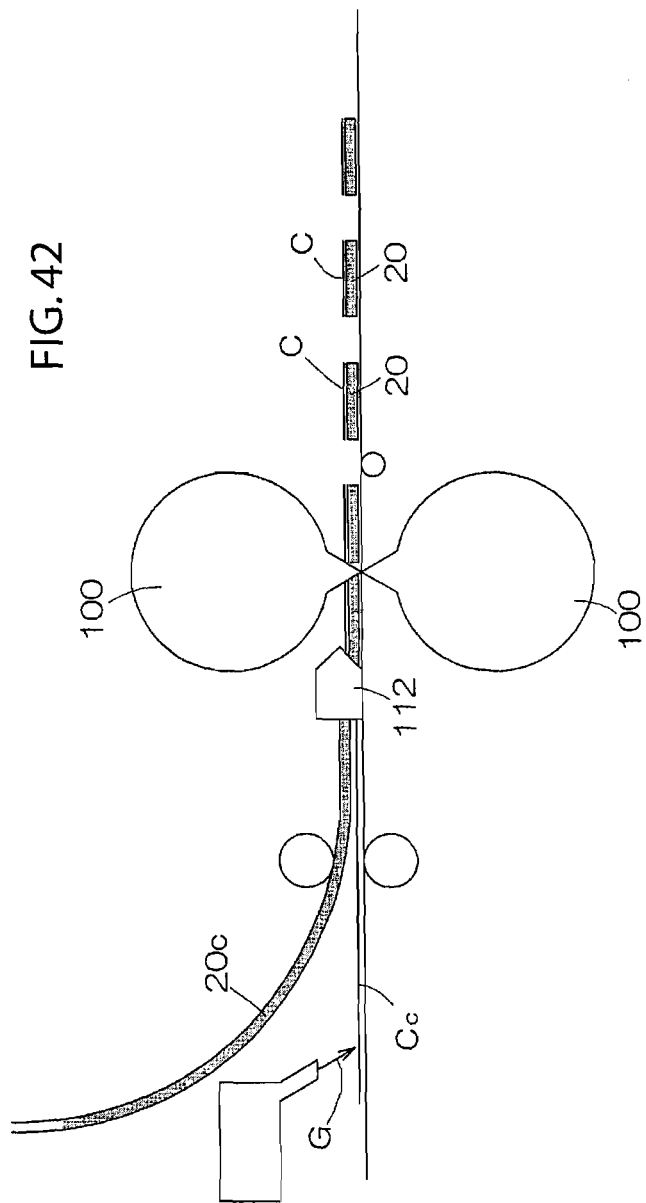
FIG. 42 is a schematic illustration for explaining the producing method of the third embodiment of a sanitary napkin
Figure 43:
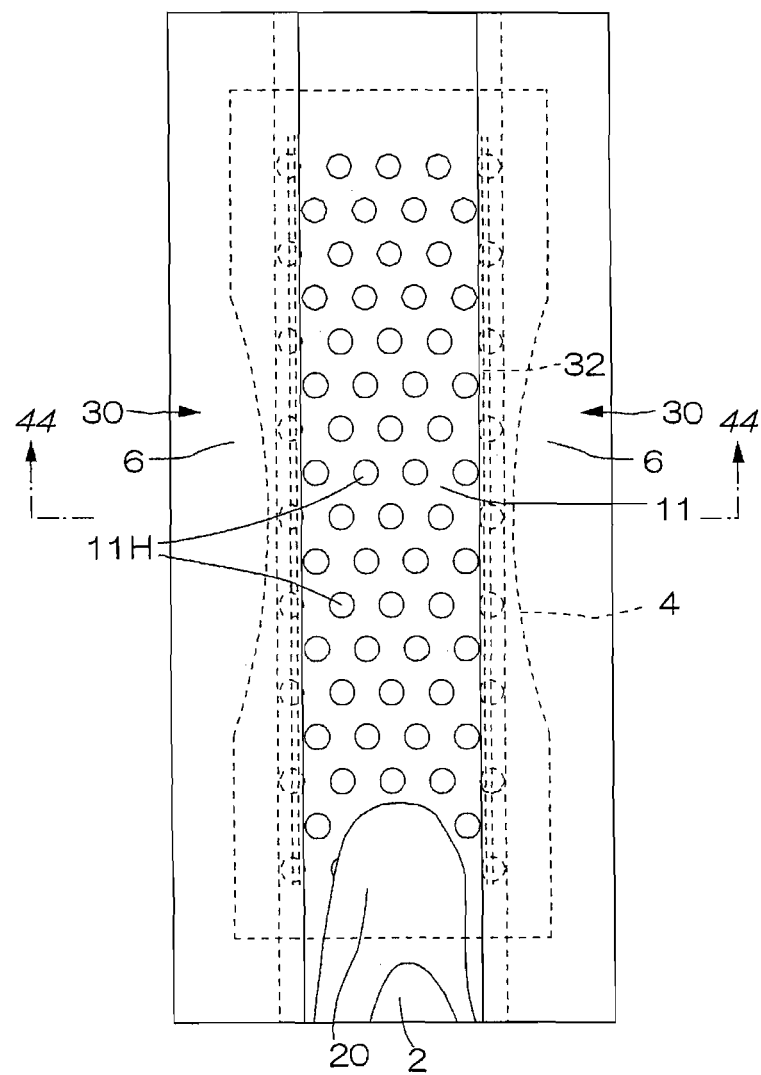
FIG. 43 is a plan view of a developed embodiment of an absorbent article.
Figure 44:
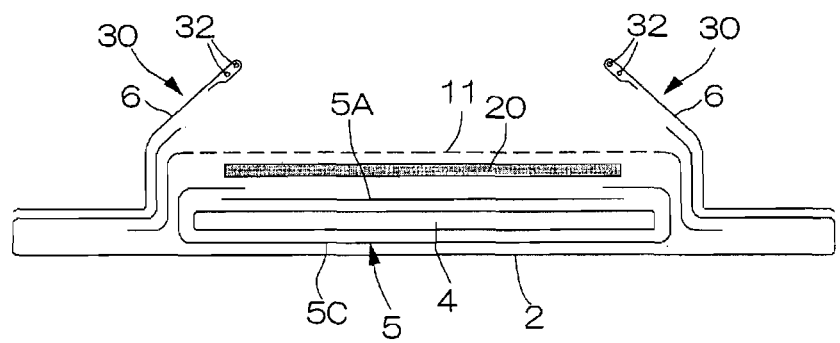
FIG. 44 is a cross section taken in the direction of the arrows along the line 44-44 of FIG. 43.
Figure 45:
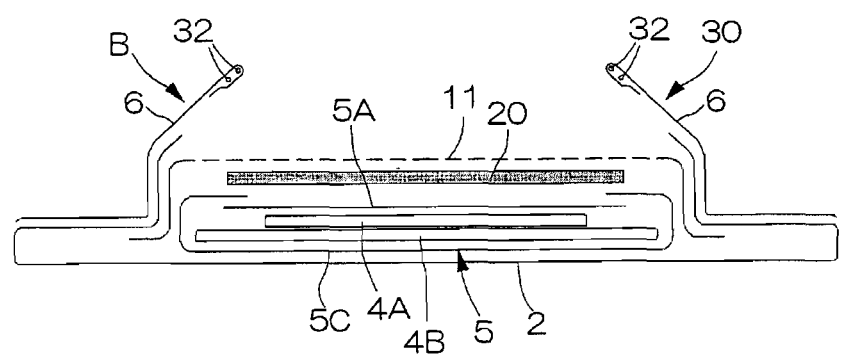
FIG. 45 is a cross section of another embodiment.
Figure 46:
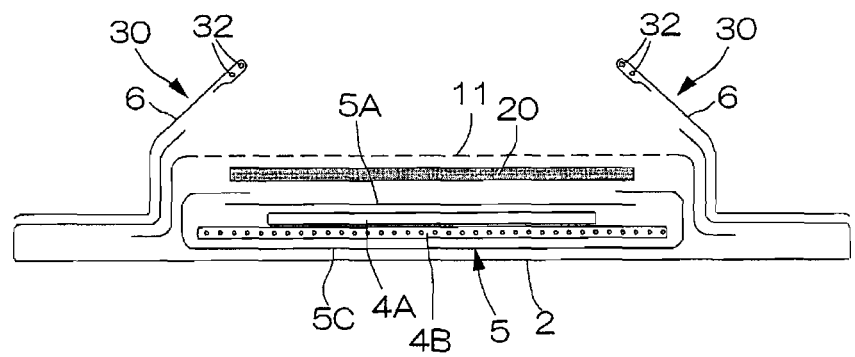
FIG. 46 is a cross section of still another embodiment.
Figure 47:
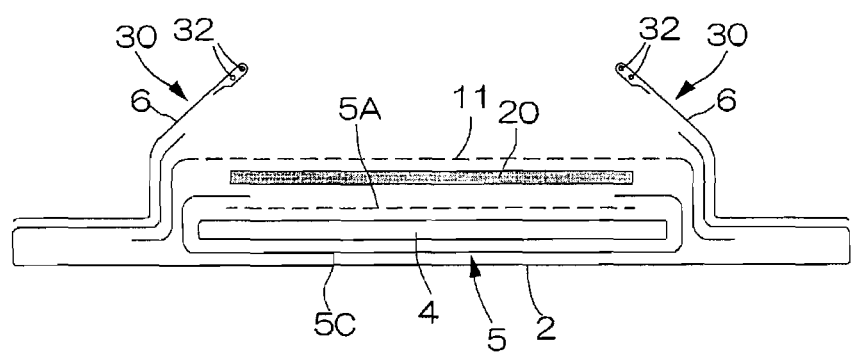
FIG. 47 is a cross section of another embodiment.
Figure 48:
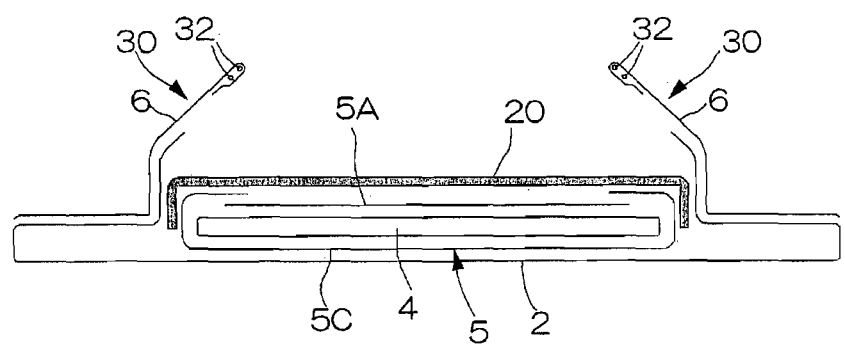
FIG. 48 is a cross section of still another embodiment.

1 . . . face sheet, 2 . . . back sheet, 10 . . . face-side second sheet, 20 . . . body fluid permeable member, AB . . . absorbent element

The invention claimed is:
1. A sanitary napkin with a tow fiber assembly, the napkin including a body fluid permeable face sheet, a back sheet, a body fluid retainable absorbent element interposed between the face sheet and the back sheet, and a body fluid permeable member which is interposed between the face sheet and the absorbent element and which includes the assembly of fibers in tows wherein
    a face-side second sheet is interposed between said face sheet and said body fluid permeable member with such a positional relation that said face-side second sheet is at least partly superposed on said body fluid permeable member and promotes body fluid permeating and protects against body fluid reversing;
    embossing is carried out on said face sheet and said face-side second sheet so as to form jogs which are depressed portions and which are projected downwardly from the under surfaces in said face sheet and said face-side second sheet so that said sheets are unified;

embossing is not carried out on said body fluid permeable member;

said jogs contact said body fluid permeable member;

said face sheet has the basis weight of 8 to 40 g/m² and the thickness of 0.2 to 1.5 mm; and said face-side second sheet is a nonwoven sheet having the basis weight of 15 to 80 g/m² and the thickness of 0.2 to 3.5 mm.

2. A sanitary napkin with a tow fiber assembly as defined in claim 1, wherein an area of said face-side second sheet is smaller than both areas of said face sheet and of said body fluid retainable absorbent element and an area of said body fluid permeable member is smaller than both the areas of said face sheet and of said body fluid retainable absorbent element.

3. A sanitary napkin with a tow fiber assembly as defined in claim 1, wherein the constituent fiber of the assembly of fibers in tows is cellulose acetate fiber.

\* \* \* \* \*

UNITED STATES PATENT AND TRADEMARK OFFICE
CERTIFICATE OF CORRECTION

PATENT NO. : 8,859,844 B2
APPLICATION NO. : 11/631226
DATED : October 14, 2014
INVENTOR(S) : Tomonari Takeuchi et al.

It is certified that error appears in the above-identified patent and that said Letters Patent is hereby corrected as shown below:

On The Title Page, item (73) Assignee should read

-- (73) Assignee: Daio Paper Corporation, Ehime (JP) --.

Signed and Sealed this
Seventeenth Day of February, 2015

Michelle K. Lee
*Deputy Director of the United States Patent and Trademark Office*